(12) United States Patent
Nock et al.

(10) Patent No.: US 10,335,122 B2
(45) Date of Patent: Jul. 2, 2019

(54) MULTI-CHAMBER TISSUE SAMPLE CUP FOR BIOPSY DEVICE

(71) Applicant: Devicor Medical Products, Inc., Cincinnati, OH (US)

(72) Inventors: Andrew Paul Nock, Dayton, OH (US); Andrew Robinson, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 16/117,391

(22) Filed: Aug. 30, 2018

(65) Prior Publication Data

US 2019/0008488 A1 Jan. 10, 2019

Related U.S. Application Data

(63) Continuation of application No. 15/829,499, filed on Dec. 1, 2017.

(Continued)

(51) Int. Cl.
*A61B 5/00* (2006.01)
*A61B 10/00* (2006.01)
(Continued)

(52) U.S. Cl.
CPC ...... *A61B 10/0096* (2013.01); *A61B 10/0275* (2013.01); *A61B 10/0283* (2013.01);
(Continued)

(58) Field of Classification Search
CPC . A61B 10/02; A61B 10/0233; A61B 10/0275; A61B 10/0283; A61B 10/0096; A61B 2010/0225; A61B 10/0266
See application file for complete search history.

(56) References Cited

U.S. PATENT DOCUMENTS

| | | | |
|---|---|---|---|
| 5,526,822 | A | 6/1996 | Burbank et al. |
| 5,928,164 | A | 7/1999 | Burbank et al. |

(Continued)

FOREIGN PATENT DOCUMENTS

| | | |
|---|---|---|
| WO | WO 2013/192606 A1 | 12/2013 |
| WO | WO 2013/192607 A1 | 12/2013 |
| WO | WO 2014/151603 A1 | 9/2014 |

OTHER PUBLICATIONS

Hahn, Markus et al., "Vacuum Assisted Breast Biopsy with Mammotome®" available Nov. 11, 2012, copyright 2013 by Devicor Medical Germany GmbH, published in Germany by Springer Medizin Verlag. 128 pages.

(Continued)

*Primary Examiner* — Max F Hindenburg
(74) *Attorney, Agent, or Firm* — Frost Brown Todd LLC

(57) ABSTRACT

A biopsy device includes a body, a needle, a cutter, and a tissue sample holder. The needle extends distally from the body. The cutter is longitudinally translatable relative to the needle and defines a cutter lumen. The tissue sample holder includes a rotatable member, an individual sample tray, and one or more bulk sample trays. The rotatable member defines a single chamber partially divided by a plurality of tray protrusions extending radially inwardly from a cylindrical wall of the rotatable member. The individual sample tray includes a single sample chamber that is configured to receive a single tissue sample. The bulk sample tray is configured to receive a plurality of tissue samples.

20 Claims, 27 Drawing Sheets

Related U.S. Application Data

(60) Provisional application No. 62/429,471, filed on Dec. 2, 2016.

(51) Int. Cl.
*A61B 10/02* (2006.01)
*B01L 3/00* (2006.01)
*B65D 25/10* (2006.01)

(52) U.S. Cl.
CPC ............ *B01L 3/508* (2013.01); *B65D 25/108* (2013.01); *A61B 10/0041* (2013.01); *A61B 2010/009* (2013.01); *A61B 2010/0225* (2013.01); *B01L 2300/0832* (2013.01); *B01L 2300/0848* (2013.01); *B01L 2300/0861* (2013.01)

(56) References Cited

U.S. PATENT DOCUMENTS

| | | | |
|---|---|---|---|
| 6,017,316 A | 1/2000 | Ritchart et al. |
| 6,086,544 A | 7/2000 | Hibner et al. |
| 6,162,187 A | 12/2000 | Buzzard et al. |
| 6,432,065 B1 | 8/2002 | Burdorff et al. |
| 6,626,849 B2 | 9/2003 | Huitema et al. |
| 6,752,768 B2 | 6/2004 | Burdorff et al. |
| 7,442,171 B2 | 10/2008 | Stephens et al. |
| 7,648,466 B2 | 1/2010 | Stephens et al. |
| 7,837,632 B2 | 11/2010 | Stephens et al. |
| 7,854,706 B2 | 12/2010 | Hibner |
| 7,914,464 B2 | 3/2011 | Burdorff et al. |
| 7,938,786 B2 | 5/2011 | Ritchie et al. |
| 8,083,687 B2 | 12/2011 | Parihar |
| 8,118,755 B2 | 2/2012 | Hibner et al. |
| 8,206,316 B2 | 6/2012 | Hibner et al. |
| 8,241,226 B2 | 8/2012 | Hibner et al. |
| 8,251,916 B2 | 8/2012 | Speeg et al. |
| 8,454,531 B2 | 6/2013 | Speeg et al. |
| 8,532,747 B2 | 9/2013 | Nock et al. |
| 8,622,924 B2 | 1/2014 | Speeg et al. |
| 8,702,623 B2 | 4/2014 | Parihar et al. |
| 8,764,680 B2 | 6/2014 | Rhad et al. |
| 8,801,742 B2 | 8/2014 | Rhad et al. |
| 8,858,465 B2 | 10/2014 | Fiebig |
| 8,938,285 B2 | 1/2015 | Fiebig et al. |
| 9,095,326 B2 | 8/2015 | Ritchie et al. |
| 9,326,755 B2 | 5/2016 | Fiebig et al. |
| 9,345,457 B2 | 5/2016 | Speeg et al. |
| 9,486,186 B2 | 11/2016 | Fiebig et al. |
| 2006/0074345 A1 | 4/2006 | Hibner |
| 2008/0214955 A1 | 9/2008 | Speeg et al. |
| 2009/0131821 A1 | 5/2009 | Speeg et al. |
| 2010/0152610 A1 | 6/2010 | Parihar et al. |
| 2010/0160819 A1 | 6/2010 | Parihar et al. |
| 2013/0053724 A1 | 2/2013 | Fiebig et al. |
| 2013/0144188 A1 | 6/2013 | Fiebig et al. |
| 2013/0218047 A1 | 8/2013 | Fiebig et al. |
| 2013/0324882 A1 | 12/2013 | Mescher et al. |
| 2014/0275999 A1 | 9/2014 | Speeg et al. |
| 2015/0065913 A1 | 3/2015 | Keller et al. |
| 2015/0327842 A1 | 11/2015 | Rhad et al. |
| 2016/0166331 A1 | 6/2016 | Leimbach et al. |
| 2016/0183928 A1 | 6/2016 | Speeg et al. |

OTHER PUBLICATIONS

International Search Report and Written Opinion for International Application No. PCT/US2017/064266, dated Mar. 28, 2018, 11 pages.

U.S. Appl. No. 15/829,499, entitled "Multi-Chamber Tissue Sample Cup for Biopsy Device," filed Dec. 1, 2017.

U.S. Appl. No. 61/566,792, filed Dec. 5, 2011.

U.S. Appl. No. 62/429,356, entitled "Functional Cover for Biopsy Device," filed Dec. 2, 2016.

U.S. Appl. No. 62/429,379, entitled "Apparatus to Allow Biopsy Sample Visualization During Tissue Removal," filed Dec. 2, 2016.

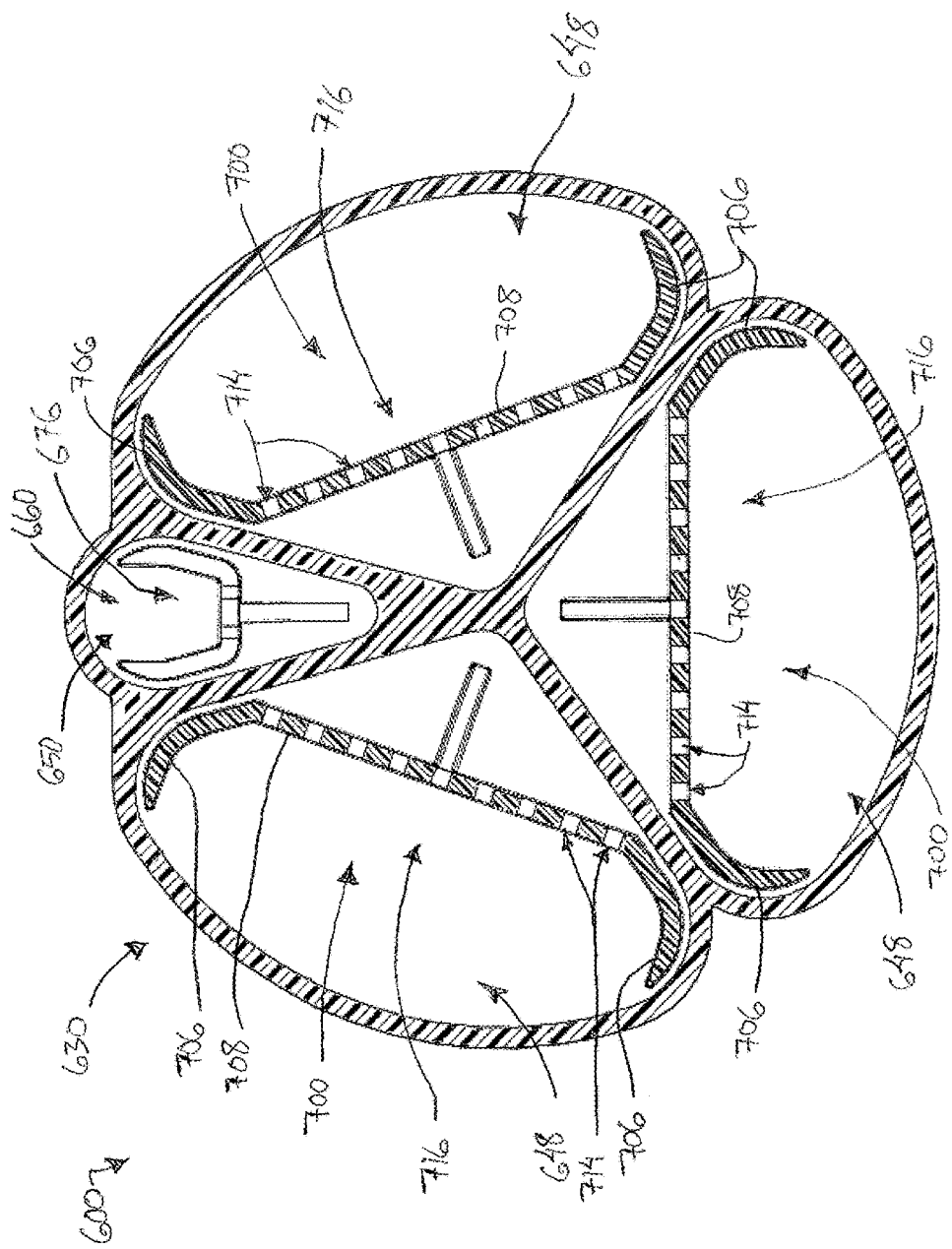

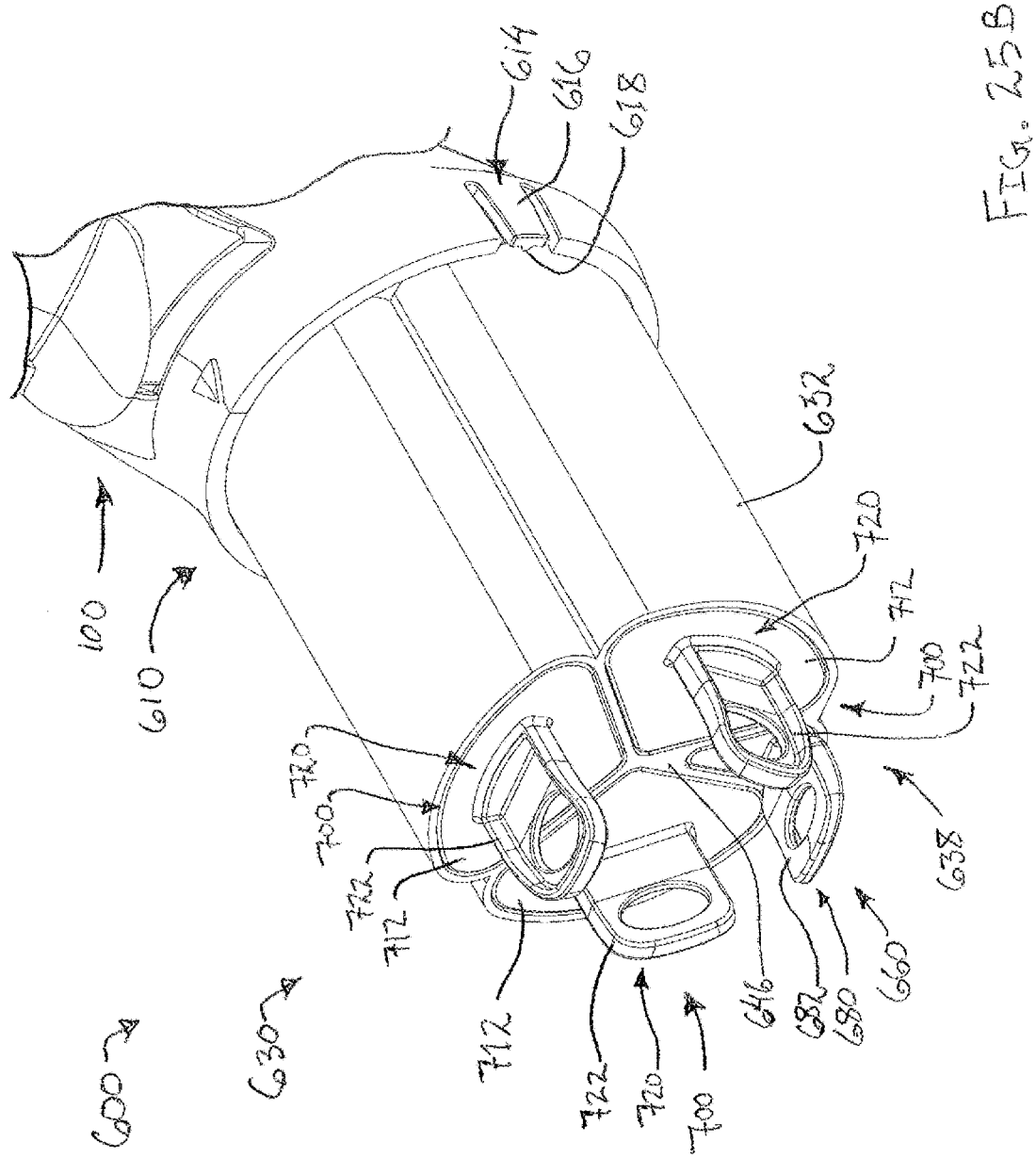

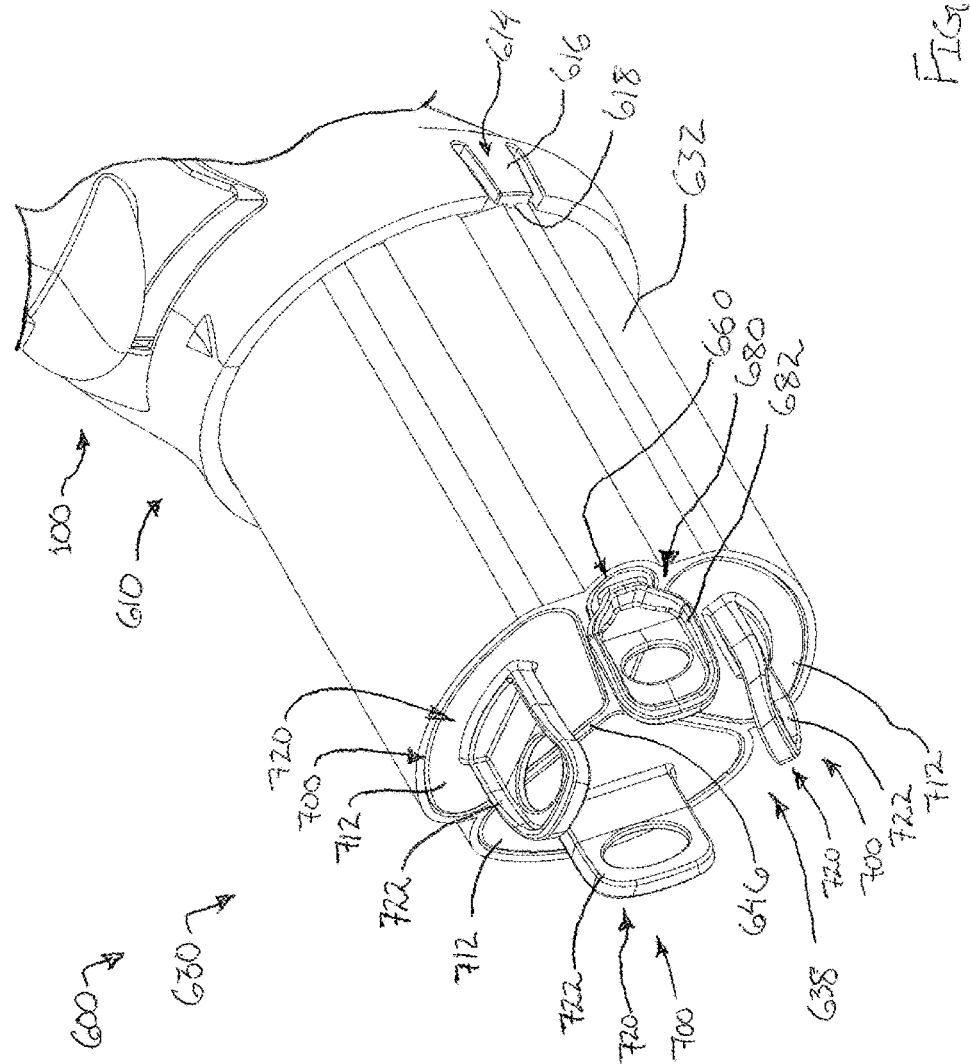

MULTI-CHAMBER TISSUE SAMPLE CUP FOR BIOPSY DEVICE

PRIORITY

The present application claims priority to US Provisional Patent Application No. 62/429,471, entitled "Multi-Chamber Tissue Sample Cup for Biopsy Device," filed on Dec. 2, 2016, the disclosure of which is hereby incorporated by reference herein in its entirety.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological).

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

The state of the art for breast biopsy is vacuum-assisted breast biopsy. A current textbook in this area is "Vacuum-Assisted Breast Biopsy with Mammotome®," available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

Biopsy devices may be used under ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following briefly describes ultrasound image guided biopsy procedures, stereotactic guided biopsy procedures and MRI guided biopsy procedures.

In an ultrasound image guided breast biopsy procedure, the operator may position an ultrasound transducer on the patient's breast and maneuver the transducer while viewing an ultrasound image display screen to locate suspicious tissue in the patient's breast. Once the operator locates the suspicious tissue, the operator may anesthetize the target region of the breast. Once the breast has been anesthetized, the operator may create an initial incision using a scalpel at a location on the exterior of the breast offset from the transducer. A needle of a breast biopsy probe disposed coaxially within an introducer cannula is then inserted into the breast through the initial incision. The operator continues to hold the ultrasound transducer with one hand while maneuvering the biopsy probe with the other hand. While viewing the ultrasound image on the display screen, the operator guides the needle to a position adjacent to the suspicious tissue. A cutter within the needle of the probe is used to remove tissue which is then conveyed either to a manual pick-up location on the breast biopsy device or to a tissue sample chamber. The needle of the breast biopsy device is then removed, leaving the introducer cannula disposed within the breast. The introducer cannula may then be used to introduce a biopsy marker cannula for deploying a biopsy site marker at the biopsy site. Once a marker has been deployed at the biopsy site, the biopsy marker cannula and the introducer cannula are both removed from the breast and the incision is closed using a medically acceptable way to close breaks in the skin.

In a stereotactic image guided breast biopsy procedure, the patient is first positioned relative to x-ray equipment, which includes a breast localization assembly. In some procedures, the patient is oriented in a prone position, with the patient lying face down on a procedure table with at least one breast hanging pendulously through an aperture in the procedure table. The breast is then compressed between a compression paddle and an x-ray receptor of a localization assembly that is positioned under the procedure table. A breast biopsy device is positioned on an automatic guide device in front of the compression paddle and between the breast and an x-ray source. Once positioning of the patient and localization of the breast are complete, a scout image is acquired with the x-ray receptor in a zero-degree angular position (i.e., the x-rays are emitted along an axis normal relative to the x-ray receptor). If the scout image indicates that the patient has been positioned in a desired position, the procedure may proceed with the acquisition of stereotactic image pairs. Stereotactic image pairs are acquired by orienting the x-ray source at various complementary angular positions relative to the x-ray receptor (e.g., +15° and −15°), with at least one x-ray image acquired at each position.

Further in the stereotactic image guided breast biopsy procedure, once a suitable stereotactic image pair is acquired, an operator may identify a target site where biopsy sampling is desired by examining the stereotactic image pair. The target site is marked on each stereotactic image and a precise location of the target site on a Cartesian coordinate system is computed using an image processing module. The computed location of the target site is then communicated to the automatic guide device. The automatic guide device is responsive to this information to position the breast biopsy probe into a position that aligns with the target site. With the breast biopsy device positioned, an operator may then fire a needle of the biopsy probe into the breast of the patient, thereby positioning the needle at the target site. A cutter within the needle of the probe is used to remove tissue, which is then conveyed either to a manual pick-up location on the breast biopsy device or to a tissue sample chamber. After the biopsy tissue is removed, a biopsy marker cannula is inserted into the needle and is used to deploy a biopsy site marker at the biopsy site. Once a marker has been deployed at the biopsy site, the needle is removed from the breast and the incision is closed using a medically acceptable way to close breaks in the skin.

In an MRI guided breast biopsy procedure, after the patient is properly positioned on the table and a targeting device (e.g., a grid and cube combination or a pillar, post and cradle support combination) has been deployed and used, a baseline MRI image is taken to verify the target location. After that, a scalpel is used to incise the skin of the breast. Next, an assembly, formed by an obturator disposed in a sleeve, is inserted through the incision to penetrate the breast tissue under the skin. In some acceptable surgical techniques, the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/obturator assembly has penetrated. In some other acceptable surgical techniques, the obturator cooperates with the breast tissue to provide a visually observable artifact in an MRI image. With both of these techniques, after the location within the breast where the biopsy is to be taken is confirmed, the obturator or the imaging rod is removed.

Further in the MRI guided breast biopsy procedure, after the obturator or imaging rod has been removed, it is replaced in the sleeve with the needle of a breast biopsy probe. A cutter within the needle of the probe is used to remove tissue, which is then conveyed either to a manual pick up location on the breast biopsy device or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

Known biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454,531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015; U.S. Pat. No. 9,095,326, entitled "Biopsy System with Vacuum Control Module," issued Aug. 4, 2015 and U.S. Pat. No. 9,326,755, entitled "Biopsy Device Tissue Sample Holder with Bulk Chamber and Pathology Chamber," issued May 3, 2016. The disclosure of each of the above-cited U.S. Patents is incorporated by reference herein.

Additionally known biopsy devices and biopsy system components are disclosed in U.S. Pub. No. 2006/0074345, entitled "Biopsy Apparatus and Method," published Apr. 6, 2006 and now abandoned; U.S. Pub. No. 2008/0214955, entitled "Presentation of Biopsy Sample by Biopsy Device," published Sep. 4, 2008; U.S. Patent Pub. No. 2009/0131821, entitled "Graphical User Interface For Biopsy System Control Module," published May 21, 2009, now abandoned; U.S. Pub. No. 2010/0152610, entitled "Hand Actuated Tetherless Biopsy Device with Pistol Grip," published Jun. 17, 2010, now abandoned; U.S. Pub. No. 2010/0160819, entitled "Biopsy Device with Central Thumbwheel," published Jun. 24, 2010, now abandoned; U.S. Pub. No. 2013/0144188, entitled "Biopsy Device With Slide-In Probe," published Jun. 6, 2013; and U.S. Pub. No. 2013/0324882, entitled "Control for Biopsy Device," published Dec. 5, 2013. The disclosure of each of the above-cited U.S. Patent Application Publications is incorporated by reference herein.

U.S. Pub. No. 2014/0275999, entitled "Biopsy device" published Sep. 18, 2014, and U.S. Pub. No. 2016/0183928, entitled "Biopsy Device," published Jun. 30, 2016, both describe some aspect of a biopsy device including a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

At several steps during tissue processing using conventional techniques and instruments, it may be necessary to manually manipulate the tissue. This manual manipulation may take time and introduce the possibility of human error causing mistakes during the processing of tissue. Any and all mistakes during the processing of tissue may make the pathological examination of the tissue much more problematic to achieve the desired goal of having an accurate diagnosis. Thus, it is understood that a desired goal of modern tissue processing is the reduction of the requirement that tissue be manually manipulated.

International Pat. Pub. No. WO 2013/192606, entitled "Biopsy Tissue Sample Transport Device and Method of Using Thereof," published on Dec. 27, 2013, describes a biopsy tissue sample transport device and method of using the same including a tissue storage assembly having a sample container, having a holding structure to hold a tissue sample, the holding structure having a sample access opening formed in a sidewall; a housing that receives the tissue storage assembly, the housing comprising an assembly insertion opening through which the tissue storage assembly is inserted into the housing; a sealing member configured to engage and substantially seal the sample access opening of the holding structure of the sample container of the tissue storage assembly; and a lid to engage and substantially seal the assembly insertion opening of the housing.

International Pat. Pub. No. WO 2013/192607, entitled "Tissue Sample Container and Methods," published on Dec. 27, 2013, describes a tissue sample container including a base having a plurality of sample holding sections, which are configured to receive a plurality of tissue samples in a given orientation and are demarcated by section walls; and a lid configured to sealingly engage the base. The sample holding sections are sized and shaped to correspond to a specific tissue sample size and shape such that the base in cooperation with the section walls, maintain the given orientation and identity of the tissue samples within respective sample holding sections.

International Pat. Pub. No. WO 2014/151603, entitled "Biopsy Device," published on Sep. 25, 2014, describes a biopsy device that includes a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 24 depicts a side cross-sectional view of the tissue sample holder of FIG. 17, the cross-section taken along line 24-24 of FIG. 17;

FIG. 25B depicts still another perspective view of the tissue sample holder of FIG. 17, with the tissue sample holder in a second bulk sample collection position; and FIG. 25C depicts yet another perspective view of the tissue sample holder of FIG. 17, with the tissue sample holder in a third bulk sample collection position.

Figure 1:
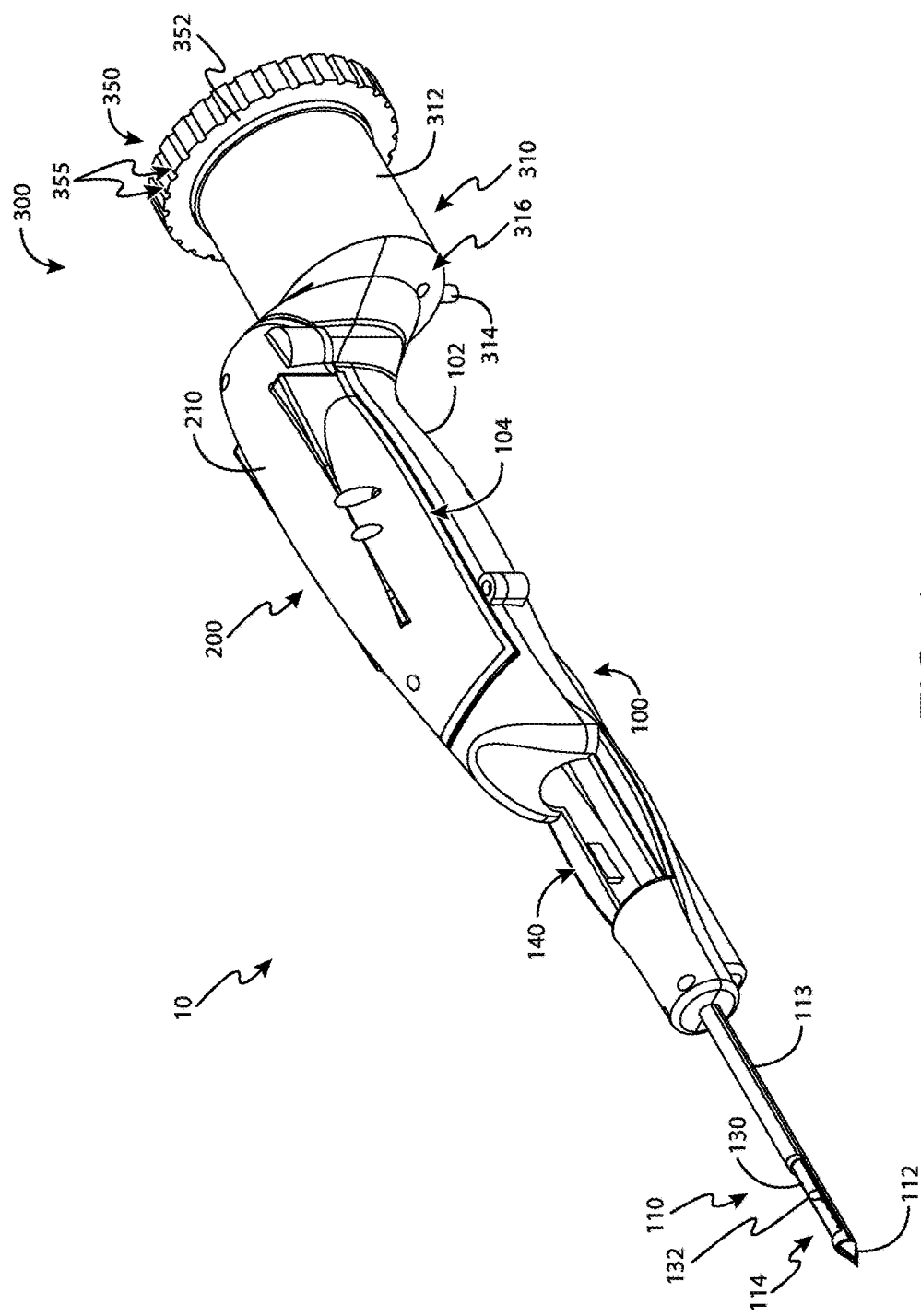
FIG. 1 depicts perspective view of an exemplary biopsy device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. EXEMPLARY BIOPSY DEVICE

FIG. 1 shows an exemplary a biopsy device (10) that may be used in a breast biopsy system including, in some examples, a vacuum control module (not shown). Biopsy device (10) of the present example comprises a probe (100) and a holster (200). A needle (110) extends distally from probe (100), and is inserted into a patient's tissue to obtain tissue samples. These tissue samples are deposited in a tissue sample holder (300) at the proximal end of probe (100), as will also be described in greater detail below.

Holster (200) of the present example is selectively attachable to probe (100) to provide actuation of various components within probe (100). In the present configuration, holster (200) is a reusable component, while probe (100) and tissue sample holder (300) are disposable. It should be understood that the use of the term "holster" herein should not be read as requiring any portion of probe (100) to be inserted into any portion of holster (200). For instance, in the present example, holster (200) includes a set of prongs (not shown) or other retention features that are received by probe (100) to releasably secure probe (100) to holster (200). Probe (100) also includes a set of resilient tabs (not shown) or other suitable release features that may be pressed inwardly to disengage the prongs, such that a user may simultaneously depress both of the tabs then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition, or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a Hall Effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured for handheld use, and be used under ultrasonic guidance. Of course, biopsy device (10) may instead be used under stereotactic guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In still other examples, biopsy device (10) can be configured to be secured to a table or other fixture without handheld operation.

In some settings, whether biopsy device (10) is handheld or mounted to a fixture, the user may capture a plurality of tissue samples with just a single insertion of needle (110) into the patient's breast. Such tissue samples may be deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

Holster (200) of the present example includes an outer housing (210) that is configured to at least partially encompass the internal components of holster (200). Although not shown, it should be understood that holster (200) of the present example includes one or more motors and/or other actuators that are configured to drive various components of probe. To communicate power or movement to probe (100), holster (200) can include one or more gears. For instance, in some examples, one or more gears at least partially extend through an opening in outer housing (210). The opening in outer housing (210) can be configured to align with a corresponding opening associated with probe (100) to thereby permit the one or more gears of holster (200) to mesh with one or more corresponding gears of probe (100).

Although not shown, it should be understood that holster (200) may also include various cables that are configured to couple holster (200) to a control module or another control feature. Suitable cables may include electrical cables, rotary drive cables, pneumatic cables, or some combination thereof. Accordingly, it should be understood that in some examples, internal components within holster (200) may be powered by electrical power (electrical cables), rotary power (rotary drive cable), and/or pneumatic power (pneumatic cables). Alternatively, in some examples the cables are omitted entirely and holster (200) can be battery powered with motors and vacuum pumps being entirely contained within holster (200).

As described above, holster (200) of the present example is configured as a reusable portion, while probe (100) is configured as a disposable portion. In some contexts, it may be desirable to maintain sterility of reusable components during a biopsy procedure. Accordingly, in some instances it may be desirable to use holster (200) in connection with certain features to maintain the sterility of holster (200), while also maintaining functionality of holster (200). Merely exemplary features and methods for maintaining the sterility of holster (200) are shown and described in U.S. Pat. App. No. 62/429,356, entitled "Functional Cover for Biopsy Device," filed on Dec. 2, 2016, the disclosure of which is incorporated by reference herein.

Probe (100) of the present example includes a needle (110) extending distally from probe (100) that is inserted into a patient's tissue to obtain tissue samples. These tissue samples are deposited in a tissue sample holder (300) at the proximal end of probe (100). In some examples, a vacuum control module (not shown) is coupled with probe (100) via a valve assembly (not shown) and tubes (not shown), which is operable to selectively provide vacuum, saline, atmospheric air, and venting to probe (100). By way of example only, the internal components of the valve assembly of the present example may be configured and arranged as described in U.S. Pat. Pub. No. 2013/0218047, entitled "Biopsy Device Valve Assembly," published Aug. 22, 2013, the disclosure of which is incorporated by reference herein.

As described above with respect to holster (200), probe (100) is selectively couplable to holster (200) so that holster (200) may provide power or otherwise actuate probe (100). In particular, probe (100) includes an outer housing (102) that includes a holster receiving portion (104) that is configured to receive holster (200). In some examples, holster receiving portion (104) includes an opening that is configured to align with a corresponding opening of holster (200). One or more gears (not shown) are exposed through the opening in outer housing (102), and are operable to drive a cutter actuation mechanism in probe (100). The one or more gears of probe (100) mesh with the one or more gears of holster (200) when probe (100) and holster (200) are coupled together. Accordingly, holster (200) may provide mechanical power or otherwise drive movement of components within probe (100) via gears of probe (100) and holster (200).

Outer housing (102) of probe (100) additionally defines a sample window (140) disposed distally on the exterior of outer housing (102) adjacent to the distal end of outer housing (102). In some examples, it may be desirable for an operator to view samples as they are collected by needle (110). For instance, and as will be described in greater detail below, in the present example tissue sample holder (300) is configured to collect tissue samples in bulk. While this configuration of tissue sample collection may enhance tissue sample capacity, the ability to visualize individual tissue samples may be reduced due to multiple tissue samples being comingled within a common space. Accordingly, sample window (140) is configured to permit an operator to visualize individual tissue samples as they are collected via needle (110). Although not shown, it should be understood that tissue sample window (140) may be equipped with seals, valves, stoppers, gates, and/or other features to selectively stop the progress of a given tissue sample through probe (100) for viewing via tissue sample window (140). In some examples, tissue sample window (140) may be constructed in accordance with the teachings of U.S. Pat. App. No. 62/429,379, entitled "Apparatus to Allow Biopsy Sample Visualization During Tissue Removal," filed on Dec. 2, 2016, the disclosure of which is incorporated by reference herein.

Needle (110) of the present example comprises a cannula (113) having a piercing tip (112), and a lateral aperture (114) located proximal to tip (112). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," filed Jun. 1, 2011, the disclosure of which is incorporated by reference herein. As another merely illustrative example, tip (112) may be configured in accordance with at least some of the teachings in U.S. Pat. Pub. No. 2013/0144188, entitled "Biopsy Device with Slide-In Probe," published Jun. 6, 2013, will issue on Nov. 8, 2016 as U.S. Pat. No. 9,486,186, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (130) having a sharp distal edge (132) is located within needle (110). Cutter (130) is operable to rotate and translate relative to needle (110) and past lateral aperture (114) to sever a tissue sample from tissue protruding through lateral aperture (114). For instance, cutter (130) may be moved from an extended position to a retracted position, thereby "opening" lateral aperture (114) to allow tissue to protrude there through; then from the retracted position back to the extended position to sever the protruding tissue.

In some examples it may be desirable to rotate needle (110) to orient lateral aperture (114) at a plurality of desired angular positions about the longitudinal axis of needle (110). In the present example, needle (110) can be rotated by a motor disposed in probe (100) or holster (200). In other examples, needle (110) is manually rotatable by a thumbwheel on probe (100) or needle hub directly overmolded onto needle (110). Regardless, it should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pat. No. 9,345,457, issued May 24, 2016, the disclosure of which is incorporated by reference herein, and/or in accordance with the teachings of any other reference cited herein.

As noted above, cutter (130) is operable to simultaneously translate and rotate relative to needle (110) to sever a tissue sample from tissue protruding through lateral aperture (114). Once severed, tissue samples are transported through cutter (130) and into tissue sample holder (300). Although not shown, it should be understood that in the present example probe (100) includes certain cutter actuation components that are configured to translate and rotate cutter (130) relative to needle (110). In some versions, the foregoing cutter actuation components are configured in accordance with at least some of the teachings of U.S. Pat. Pub. No.

2008/0214955, the disclosure of which is incorporated by reference herein. As yet another merely illustrative example, cutter (130) may be rotated and/or translated using one or more pneumatic motors and/or pneumatic actuators, etc. Still other suitable ways in which cutter (130) may be actuated will be apparent to those of ordinary skill in the art in view of the teachings herein.

II. EXEMPLARY TISSUE SAMPLE HOLDER

Figure 2:
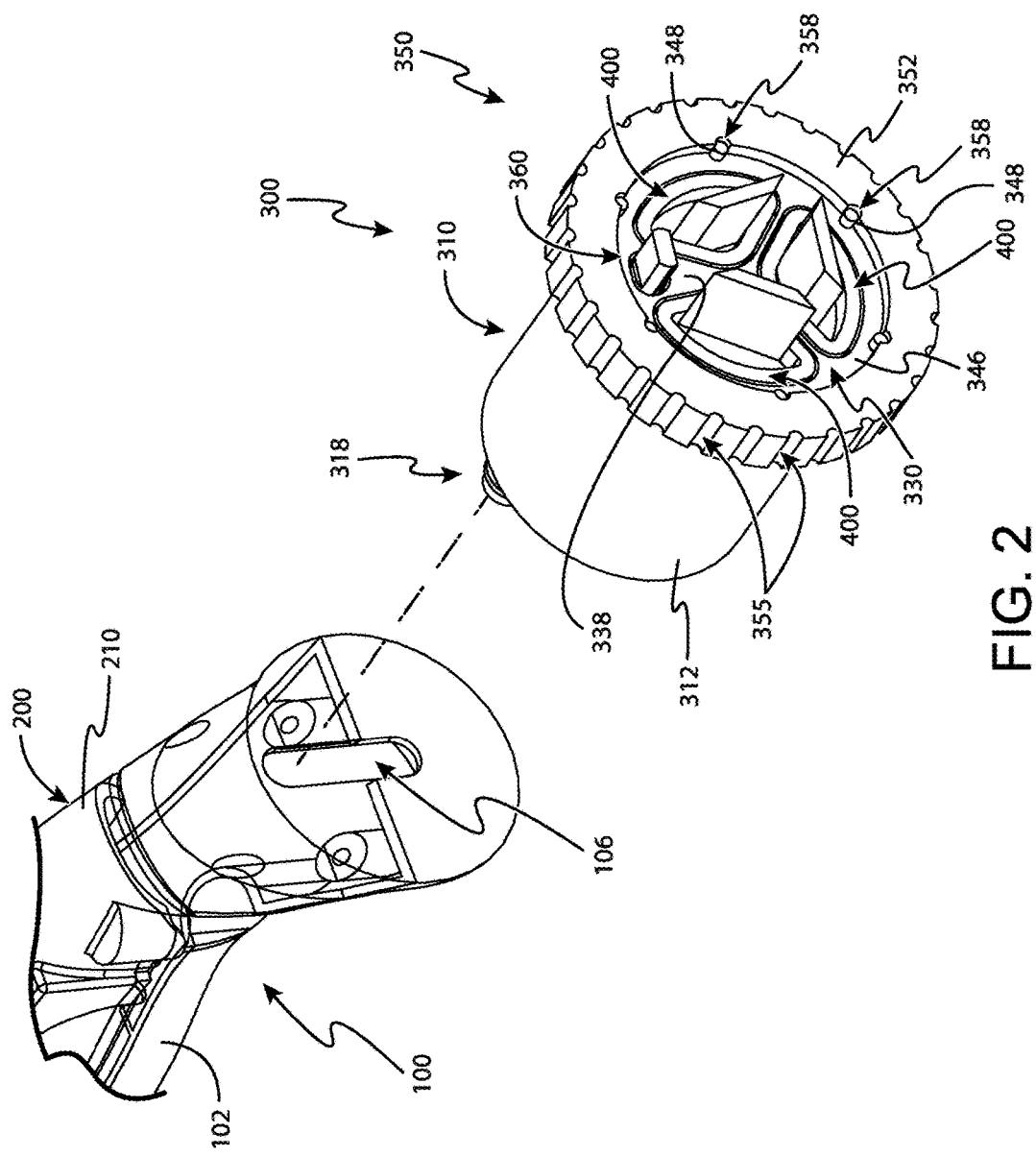
FIG. 2 depicts a perspective view of a tissue sample holder of the biopsy device of FIG. 1, with the tissue sample holder decoupled from a probe of the biopsy device.

Tissue sample holder (300) is selectively coupleable to the proximal end of probe (100). As best seen in FIG. 2, probe (100) comprises an elongate slot (106) that is configured to receive at least a portion of tissue sample holder (300). As will be described in greater detail below, slot (106) permits tissue sample holder (300) to communicate with cutter (130) such that tissue samples can be communicated through cutter (130) and into tissue sample holder (300). In some examples, vacuum and mechanical motion may also be communicated through slot (106) to tissue sample holder (300). In such examples, vacuum is provided to create a fluid circuit through tissue sample holder (300) that pulls tissue samples from cutter (130) and into tissue sample holder (300). Mechanical features may also be provided to actuate tissue sample holder (300) as will be described in greater detail below.

Tissue sample holder (300) of the present example is configured to operate in two discrete sample collection modes—a bulk tissue collection mode and an individual tissue collection mode. As will be understood, by having such a configuration, tissue sample holder (300) provides enhanced flexibility during a biopsy procedure. For instance, an operator may desire to collect tissue sample in a bulk configuration when the operator is removing large quantities of tissue from a patient without a significant interest in analyzing individual samples. However, at various points during the procedure, an operator may desire to have enhanced analysis of an individual tissue sample (e.g., to determine whether tissue sample acquisition is being performed at the margins of a lesion). Thus, it may be desirable to switch from the bulk tissue collection mode to the individual tissue collection mode to conduct further analysis of an individual tissue sample.

Figure 3:
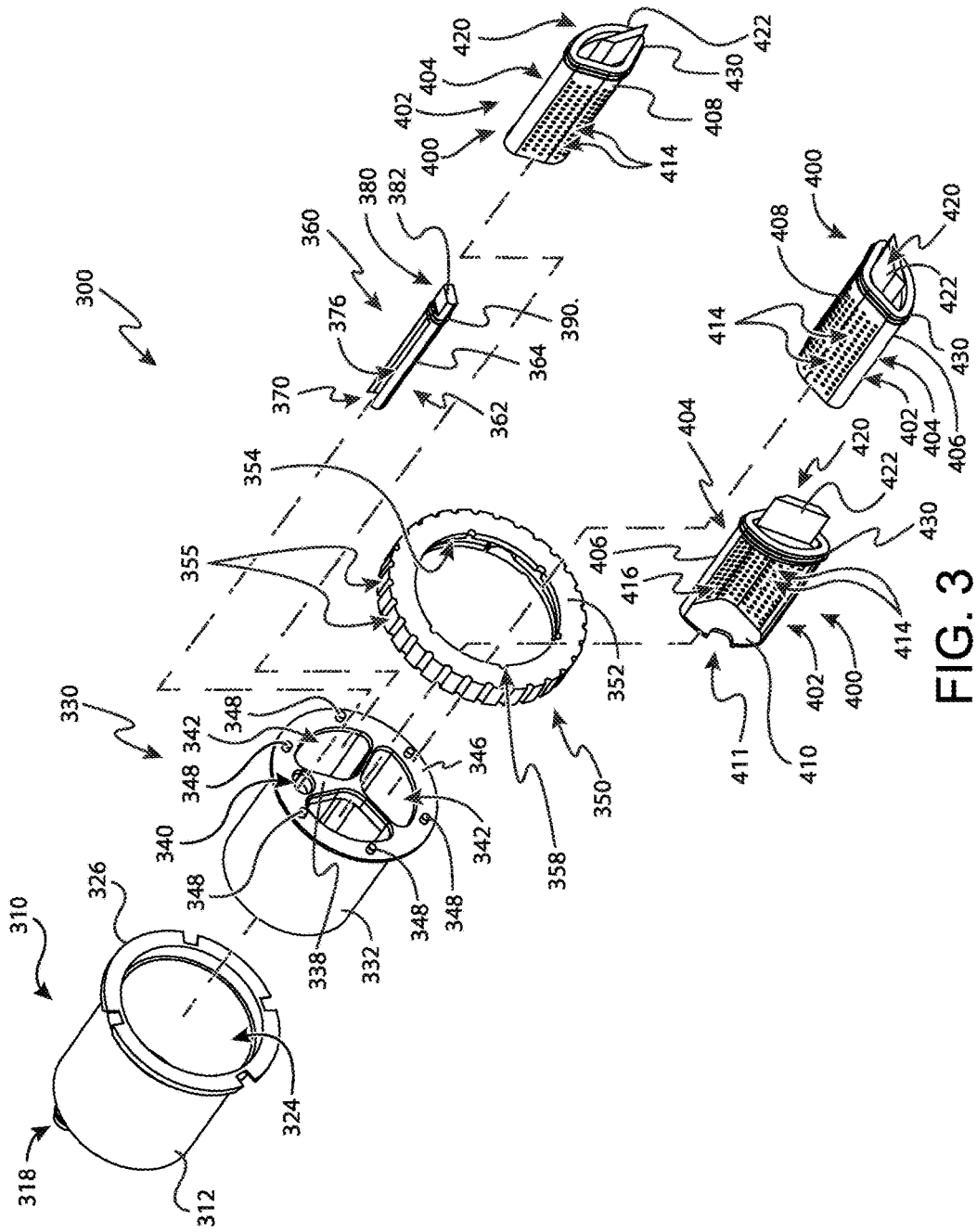
FIG. 3 depicts a perspective exploded view of the tissue sample holder of FIG. 2.

As best seen in FIG. 3, tissue sample holder comprises an outer cup (310), a rotatable member (330), a manual rotation wheel (350), an individual sample tray (360), and three bulk sample trays (400). As will be described in greater detail below, outer cup (310) is configured to receive at least a portion of rotatable member (330), manual rotation wheel (350), and trays (360, 400). With this configuration, outer cup (310) is generally secured to probe (100) and therefore remains fixed relative to probe (100) while rotatable member (330) is rotatable relative to outer cup (310) and probe (100) via manual rotation wheel (350).

Figure 4:
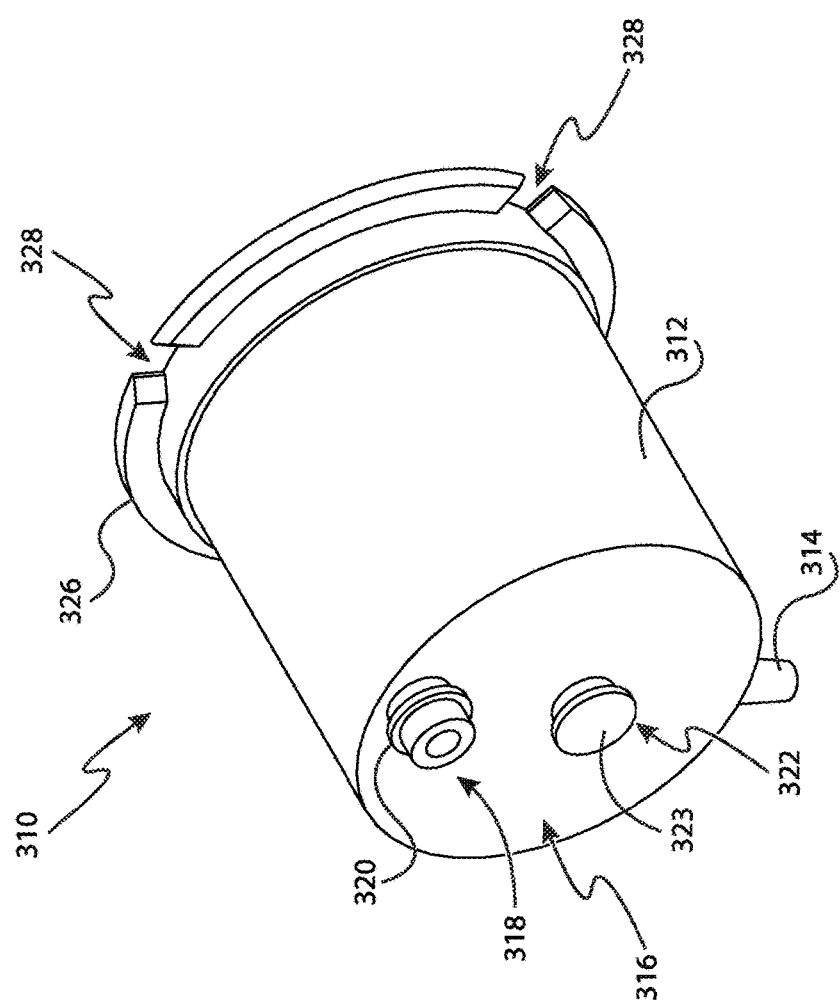
FIG. 4 depicts a perspective view of an outer cup of the tissue sample holder of FIG. 2.

As best seen in FIGS. 3 and 4, outer cup (310) defines a generally cylindrical cup that is configured to receive rotatable member (320). Outer cup (310) comprises a cylindrical body (312), a distal wall (316), an open proximal end (324), and a proximal flange (326). Cylindrical body (312) includes a vacuum port (314) adjacent to distal wall (316) and extending downwardly from cylindrical body (312). Vacuum port (314) is generally in communication with the interior of outer cup (310) defined by cylindrical body (312). As will be described in greater detail below, vacuum port (314) permits communication of vacuum to tissue sample holder (300) to create a fluid circuit that pulls tissue samples from cutter (130) and into tissue sample holder (300). Additionally, it should be understood that in some circumstances, excess liquids such as blood, saline, etc. may be evacuated from tissue sample holder (300) via vacuum port (314).

Distal wall (316) includes a tissue port (318), and a mechanical ground feature (322). Tissue port (318) extends distally from distal wall (316) is configured to communicate with the proximal end of cutter (130) to transport tissue samples from cutter (130) into tissue sample holder (300). In addition, tissue port (318) comprises a flange feature (320) that is configured to engage elongate slot (106) in probe (100). As will be understood, flange feature (320), in cooperation with mechanical ground feature (322), generally couples outer cup (310) to probe (100) via engagement between flange feature (320) and elongate slot (106) of probe (100).

Mechanical ground feature (322) extends distally from distal wall (316) of outer cup (310). Mechanical ground feature (322) includes a circular flange feature (323) that extends outwardly relative to the distal extension of mechanical ground feature (322). As similarly discussed above with respect to flange feature (320) of tissue port (318), flange feature (323) of mechanical ground feature (322) is configured to engage elongate slot (106) of probe (100) to secure the position of outer cup (310) relative to probe (100). Thus, it should be understood that mechanical ground feature (322) secures outer cup (310) to probe (100). In addition, mechanical ground feature (322) acts cooperatively with tissue port (318) to act as a mechanical ground to prevent rotation of outer cup (310) relative to probe (100). Although flange features (320, 323) of tissue port (318) and mechanical ground feature (322) are used to couple outer cup (310) to probe (100) in the present example, it should be understood that in other examples numerous other coupling features may be incorporated into outer cup (310) and/or probe (100) as will be apparent to those of ordinary skill in the art in view of the teachings herein.

Open proximal end (324) is defined by the proximal end of cylindrical body (312). Thus, it should be understood that open proximal end (324) is configured to receive rotatable member (330) proximally relative to outer cup (310). Proximal flange (326) is positioned adjacent to open proximal end (324) and extends outwardly from cylindrical body (312). As will be described in greater detail below, proximal flange (326) is generally configured to receive manual rotation wheel (350) to rotatably fasten manual rotation wheel (350) to outer cup (310). As will also be described in greater detail below, rotatable member (330) is secured to manual rotation wheel (350). Thus, it should be understood that proximal flange (326) is configured to secure both manual rotation wheel (350) and rotatable member (330) to outer cup (310), while permitting rotation of manual rotation wheel (350) and rotatable member (330) relative to outer cup (310).

Proximal flange (326) further includes a plurality of indexing features (328) angularly spaced around the perimeter of proximal flange (326). Indexing features (328) are generally configured to engage with at least a portion of manual rotation wheel (350) to bias rotation of rotatable member (330) toward certain predetermined positions. As will be described in greater detail below, each predetermined position generally corresponds to a given sample tray (360, 400) being indexed with cutter (130). Although indexing features (328) of the present example are generally shown as gaps or openings in proximal flange (326), it should be understood that in other examples indexing features (328) may take on a variety of other forms.

Figure 5:
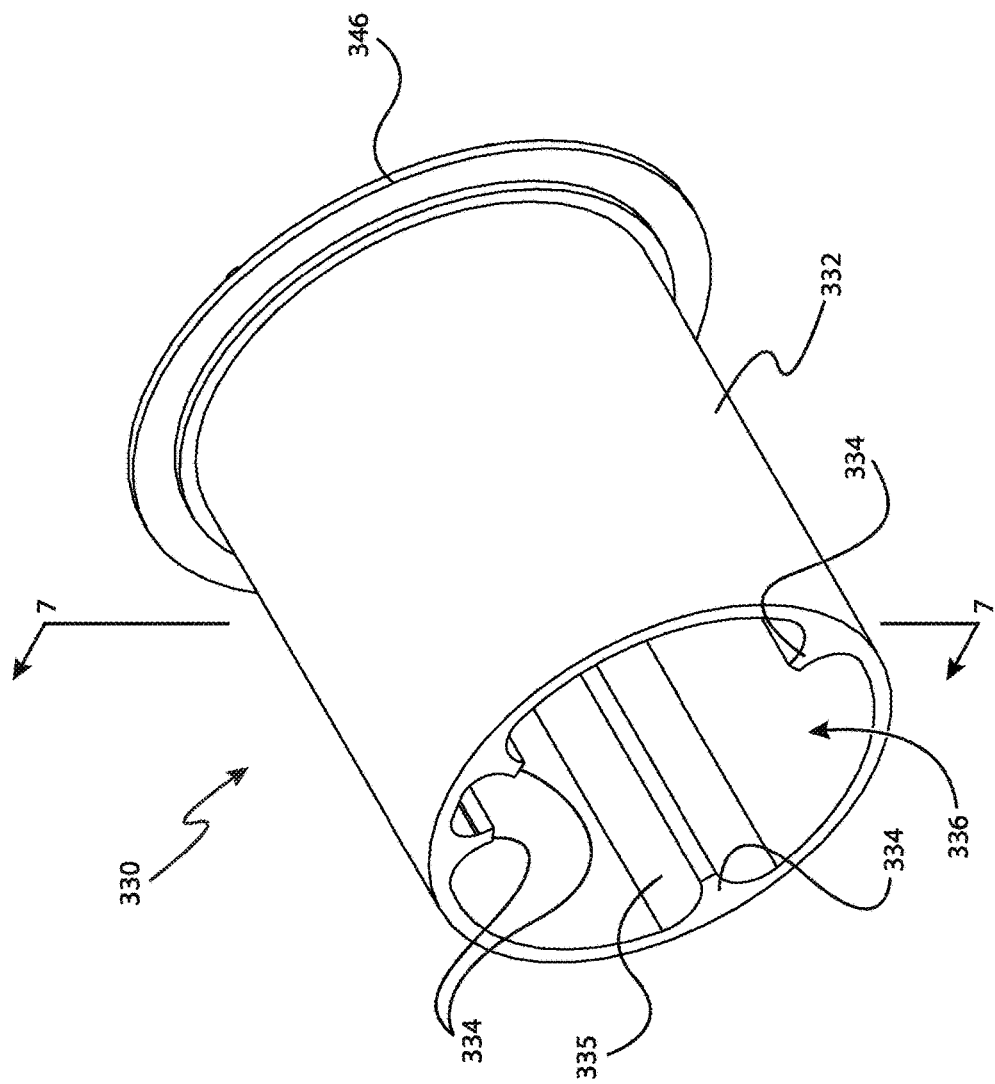
FIG. 5 depicts a perspective view of a rotatable member of the tissue sample holder of FIG. 2.
Figure 6:
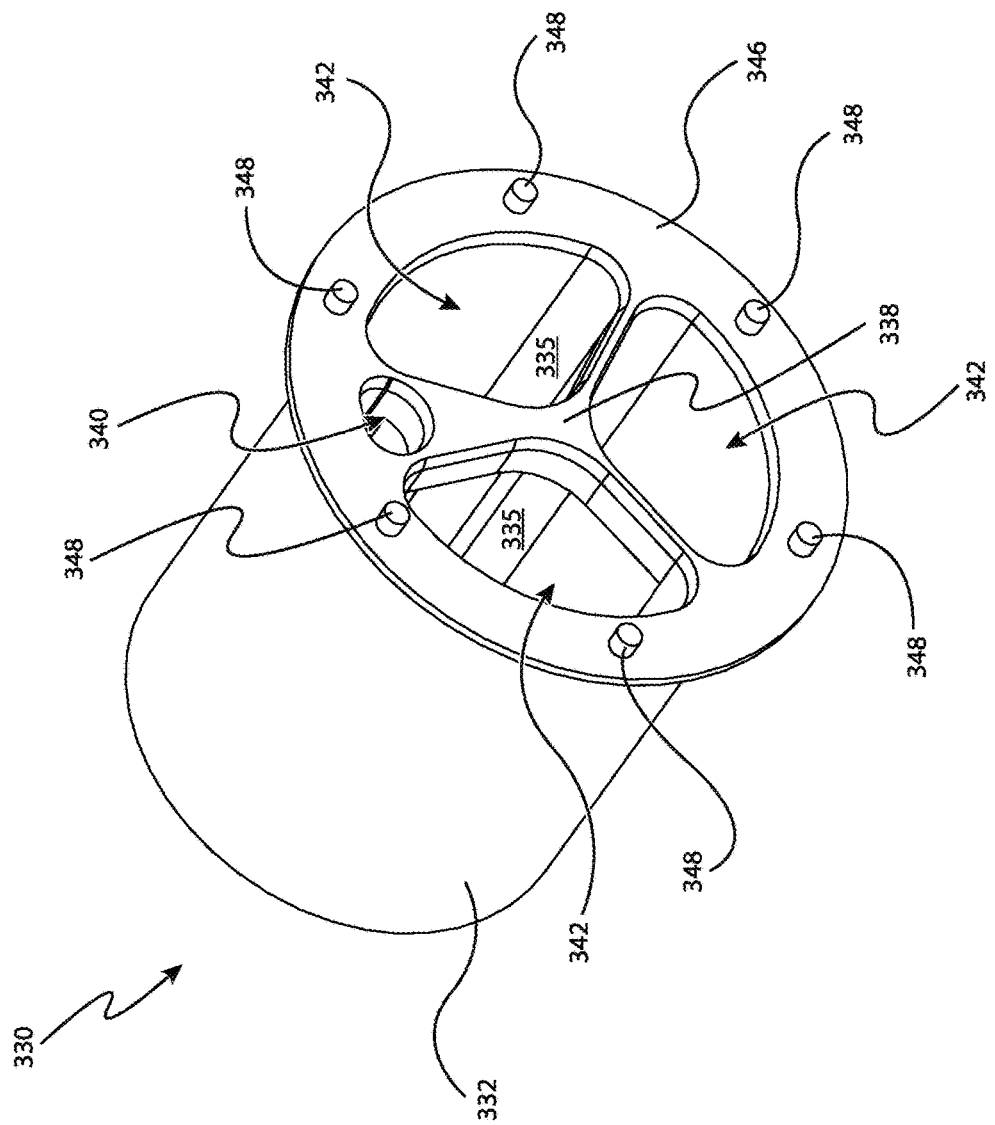
FIG. 6 depicts another perspective view of the rotatable member of FIG. 5.
Figure 7:
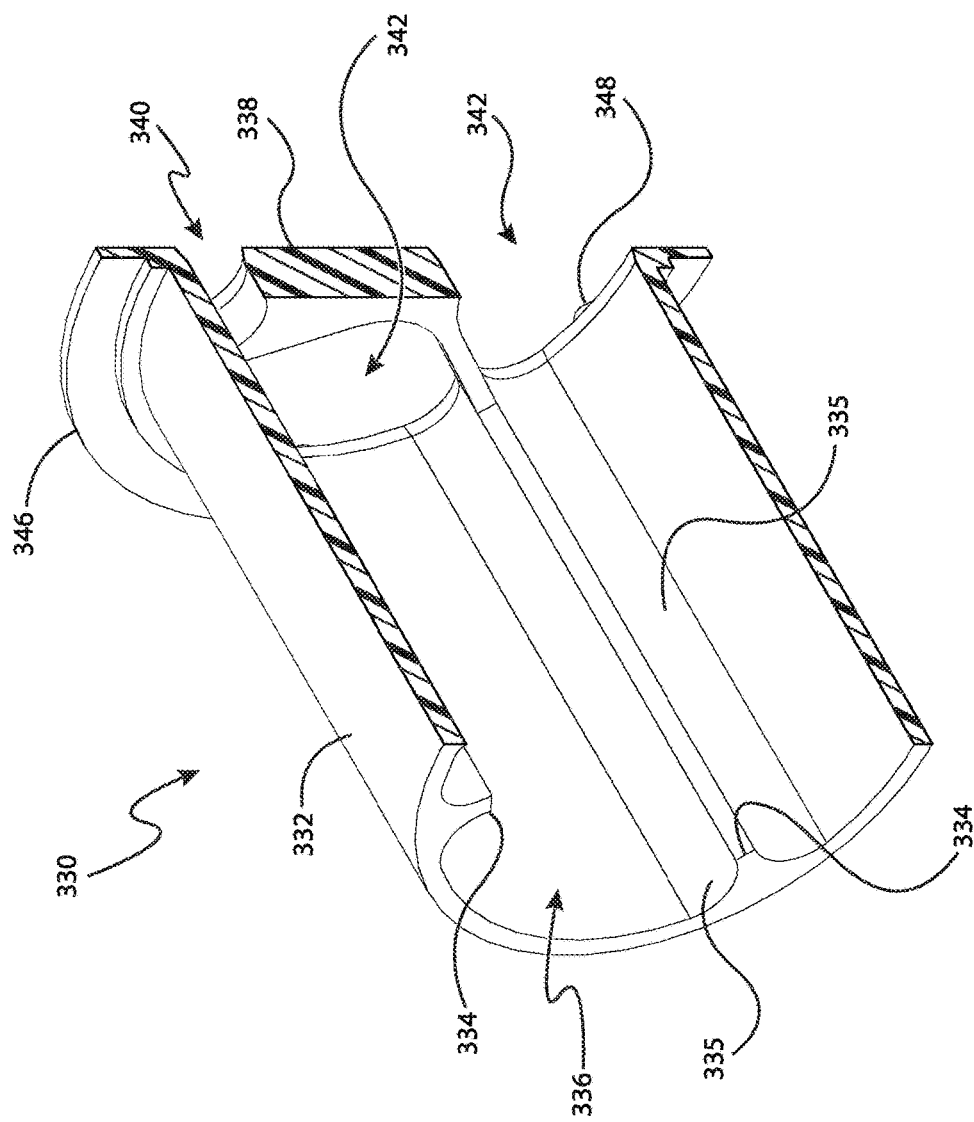
FIG. 7 depicts a perspective cross-sectional view of the rotatable member of FIG. 5, the cross-section taken along line 7-7 of FIG. 5.

FIGS. 5-7 show rotatable member (330) in greater detail. As can be seen, rotatable member (330) comprises a cylindrical wall (332), an open distal end (336), and a proximal wall (338). Cylindrical wall (332) comprises a generally hollow cylindrical shape extending between open distal end (336) and proximal wall (338). The interior of cylindrical wall (332) includes a plurality of tray protrusions (334) extending from open distal end (336) to proximal wall (338). Each tray protrusion (334) also extends radially inwardly into the interior space defined by cylindrical wall (332). Thus, cylindrical wall (332) defines a single interior space that is at least partially divided by tray protrusions (334). Tray protrusions (334) are angularly spaced around the interior circumference of cylindrical wall (332). The angular spacing of each tray protrusion (334) relative to adjacent tray protrusions (334) corresponds to a width of either individual sample tray (360) or bulk sample tray (400). In addition, each tray protrusion (334) is integrated into cylindrical wall (332) by a radiused surface (335) such that each tray protrusion (334) progressively extends inwardly from the inner surface of cylindrical wall (332). Thus, the two adjacent tray protrusions (334) and the radius of cylindrical wall (332) together define a semi-ovular shape that is configured to receive either individual sample tray (360) or bulk sample tray (400), depending on the angular separation between each adjacent tray protrusion (334). Because each tray protrusion (334) extends inwardly toward the center of cylindrical wall (332), it should be understood that each tray protrusion (334) is also configured to secure a corresponding individual sample tray (360) or bulk sample tray (400) to cylindrical wall (332), as will be described in greater detail below.

As best seen in FIG. 6, proximal wall (338) is disposed on the proximal end of cylindrical wall (332), covering the proximal end of cylindrical wall (332). Although the proximal end of cylindrical wall (332) is generally closed by proximal wall (338), proximal wall (338) defines a plurality of openings (340, 342) therein. In particular, proximal wall (338) defines a single individual tray opening (340) and three bulk tray openings (342). Individual tray opening (340) is generally oval-shaped. As will be described in greater detail below, individual tray opening (340) is configured to receive individual sample tray (360). Each bulk tray opening (342) is generally pie-shaped. As will also be described in greater detail below, each bulk tray opening (342) is configured to receive a single bulk sample tray (400). Although proximal wall (338) of the present example is shown as having a single individual tray opening (340) and three bulk tray openings (342), it should be understood that in other examples numerous other configurations can be used. For instance, in some examples proximal wall (338) defines a single bulk tray opening (342) and a plurality of individual tray openings (340). Of course, in other examples proximal wall (338) defines any other suitable number of individual tray openings (340) or bulk tray openings (342).

As best seen in FIG. 7, individual tray opening (340) and each bulk tray opening (342) is positioned to be adjacent to two corresponding tray protrusions (334) of cylindrical wall (332). In particular, individual tray opening (340) is positioned with a corresponding tray protrusion (334) adjacent to each outer corner of the oval shape of individual tray opening (340). Similarly, each bulk tray opening (342) is positioned with a corresponding tray protrusion (334) adjacent to each outer corner of the general pie shape of each bulk tray opening (342). As will be described in greater detail below, this configuration generally permits tray protrusions (334) to act as tracks or retaining features for individual sample tray (360) or each bulk sample tray (400) as individual sample tray (360) or each bulk sample tray (400) is received within a corresponding individual tray opening (340) or bulk tray opening (342).

Returning to FIG. 6, proximal wall (338) further defines a proximal flange (346) extending outwardly from the outer diameter of cylindrical wall (332). As will be described in greater detail below, proximal flange (346) is generally configured to be engaged by manual rotation wheel (350) along with proximal flange (326) of outer cup (310). As will be understood, this configuration generally permits manual rotation wheel (350) to couple rotatable member (330) to outer cup (310), while permitting rotatable member (330) to rotate relative to outer cup (310).

Proximal flange (346) of rotatable member (330) further comprises a plurality of lock protrusions (348). Lock protrusions (348) extend proximally from proximal flange (346) and are spaced angularly around the perimeter of proximal flange (346). Lock protrusions (348) are configured to engage at least a portion of manual rotation wheel (350). As will be described in greater detail, engagement between lock protrusions (348) and at least a portion of manual rotation wheel (350) provides a mechanical ground between rotatable member (330) and manual rotation wheel (350) to thereby associate rotational movement of manual rotation wheel (350) with rotational movement of rotatable member (330). Although the present example is shown as including six lock protrusions (348), it should be understood that in other examples any suitable number of lock protrusions (348) are used. Although each lock protrusion (348) is shown as having a generally cylindrical shape, it should be understood that in other examples any other suitable shape can be used. In addition, although lock protrusions (348) are shown and described herein as protruding from proximal flange (346), it should be understood that in other examples lock protrusions (348) can be indented into proximal flange (346).

Figure 8:
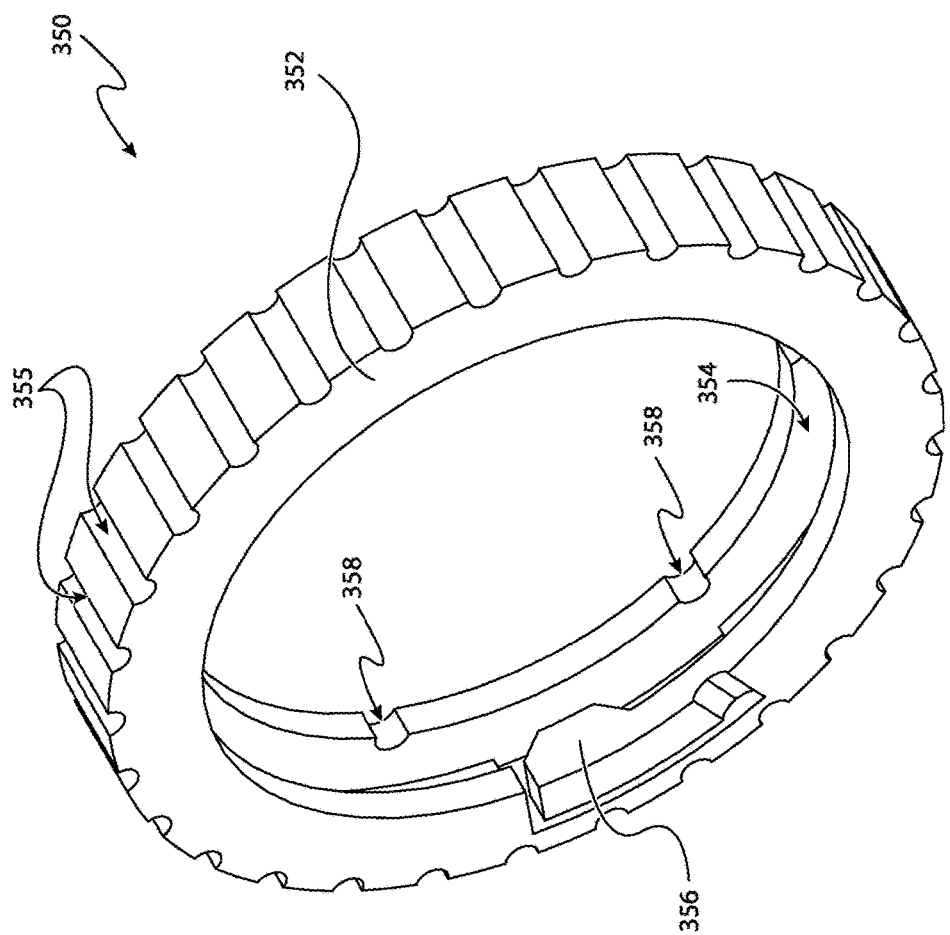
FIG. 8 depicts a perspective view of a manual rotation wheel of the tissue sample holder of FIG. 2.

FIG. 8 shows manual rotation wheel (350) in detail. As can be seen, manual rotation wheel (350) comprises a ring-shaped body (352) that defines a receiving channel (354). As described above, manual rotation wheel (350) is generally configured to engage with proximal flange (326) of outer cup (310) and proximal flange (346) of rotatable member (330) to rotatably secure rotatable member (330) to outer cup (310). This configuration permits manual rotation wheel (350) to drive rotation of rotatable member (330) and thereby index sample trays (360, 400) with cutter (130).

To promote gripping of manual rotation wheel (350), body (352) includes a plurality of grip features (355). Grip features (355) in the present example are shown as a plurality of axially extending recesses angularly spaced around the outer perimeter of body (352). In other examples, grip features (355) can comprise any other suitable feature configured to enhance grip such as a knurled surface, a rubberized surface, a texturized surface, etc.

To receive flanges (326, 346) as described above, body (352) includes receiving channel (354) extending entirely around the interior of body (352). Accordingly, it should be understood that the axial width of body (352) is configured to be wide enough to accommodate both flanges (326, 346) within receiving channel (354), while permitting flange (326) of outer cup (310) to be freely rotatable within receiving channel (354).

As described above, proximal flange (326) of outer cup (310) includes a plurality of indexing features (328) disposed about the axial perimeter of proximal flange (326). Body (352) of manual rotation wheel (350) correspondingly includes a resilient feature (356) that is configured to engage indexing features (328) of proximal flange (326). In particular, resilient feature (356) is resiliently biased inwardly into receiving channel (354) to engage each indexing feature (328) as manual rotation wheel (350) is rotated relative to outer cup (310). This configuration permits manual rotation wheel (350) to be biased toward certain predetermined positions as manual rotation wheel (350) is rotated relative to outer cup (310). This configuration in turn biases rotatable member (330) toward certain predetermined positions relative to outer cup (310). As will be described in greater detail below, such predetermined positions correspond to each sample tray (360, 400) being indexed with cutter (130).

As described above, proximal flange (346) of rotatable member (330) includes a plurality of lock protrusions (348) to lock rotation of rotatable member (330) relative to manual rotation wheel (350). Accordingly, body (352) of manual rotation wheel (350) includes a plurality of lock recesses (358) that correspond to each lock protrusion (354) of proximal flange (346). As can be seen in FIG. 8, each lock recess (358) is positioned axially around the interior of body (352) with an axial spacing corresponding to the axial spacing of lock protrusions (348). Thus, it should be understood that each lock recess (358) is configured to receive a corresponding lock protrusion (348) of proximal flange (346). As described above, lock protrusions (348) may take on a variety of forms that differ from mere cylindrical protrusions. Accordingly, it should be understood that in some examples, lock recesses (358) can likewise take on a variety of alternative corresponding forms as will be apparent to those of ordinary skill in the art in view of the teachings herein.

Figure 9:
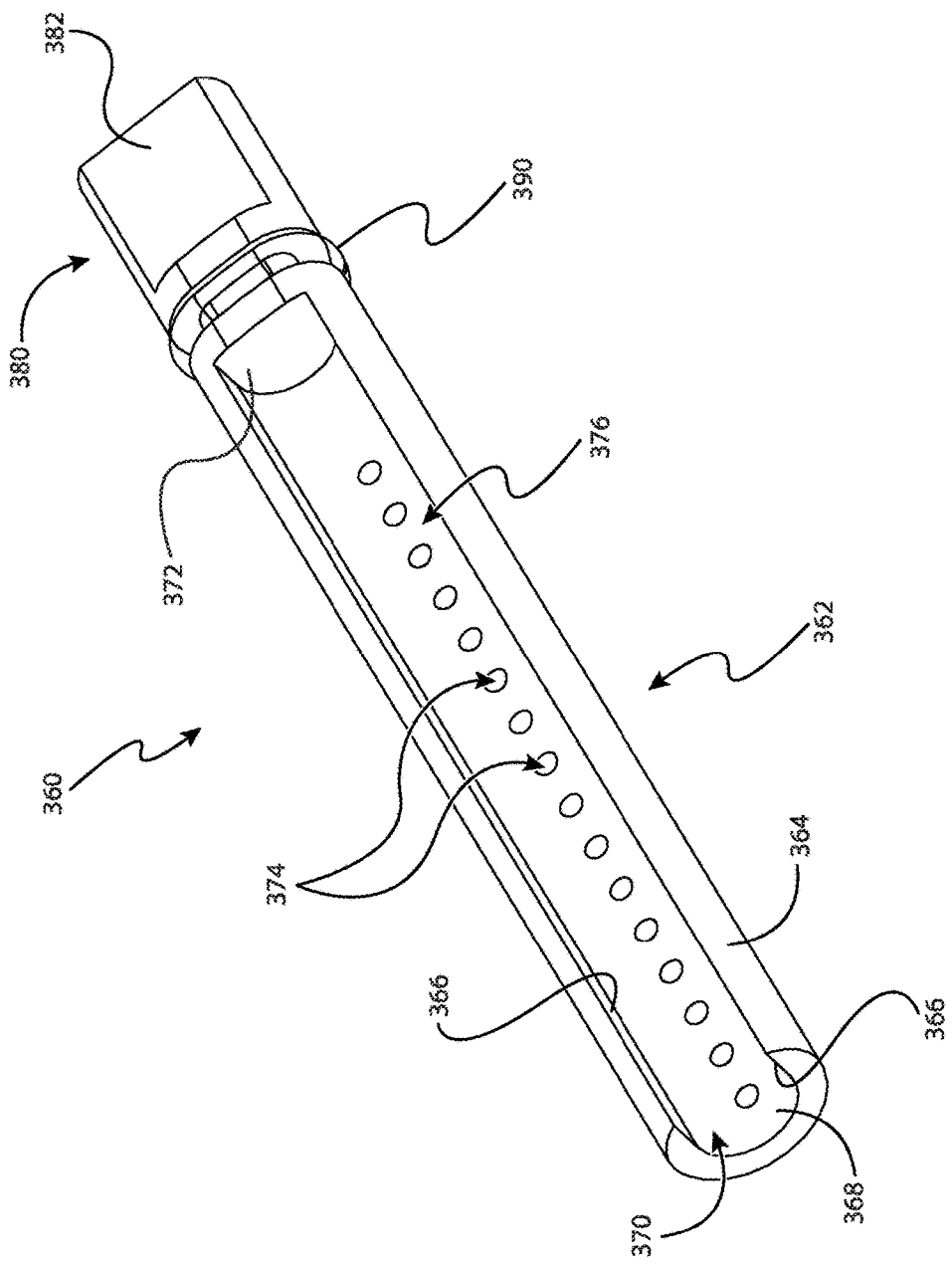
FIG. 9 depicts a perspective view of an individual sample tray of the tissue sample holder of FIG. 2.

FIG. 9 shows individual sample tray (360) in greater detail. As will be understood, individual sample tray (360) is generally configured to receive only one single tissue sample therein. It should be understood that in some contexts the terms "individual" and "single tissue sample" referred to herein is related to the transverse cross-section of individual sample tray (360). Accordingly, it should be understood that in some examples individual sample tray (360) can receive multiple tissue samples. For instance, in some examples individual sample tray (360) has an extended length such that multiple tissue samples can be received within individual sample tray (360) in a stacked end-to-end configuration despite the transverse cross-section of individual sample tray (360) being configured to receive a single tissue sample.

Individual sample tray (360) comprises a tray portion (362), a handle portion (380), and a seal (390) disposed between tray portion (362) and handle portion (380). Tray portion (362) includes a strip (364) that defines a generally oval-shaped external cross-section that corresponds to the oval shape of individual tray opening (340) of rotatable member (330). Strip (364) further defines an open distal end (370), a pair of sidewalls (366), a floor (368), and a back wall (372). Sidewalls (366), floor (368), and back wall (372) generally define a tissue sample chamber (376) that is configured to receive a single tissue sample though open distal end (370).

Strip (364) further defines a longitudinal length. In the present example this longitudinal length is approximately two and a half times greater than the length of lateral aperture (114). Thus, it should be understood that even though individual sample tray (360) is generally configured to receive a single tissue sample, in some examples multiple tissue samples can be received within individual sample tray (360) in a stacked end-to-end configuration due to the longitudinal length of strip (364). Of course, in other examples strip (364) has a longitude length that is approximately equivalent to the length of lateral aperture (114). In such examples, individual sample tray (360) can only receive a single tissue sample without compressing one or more of the tissue samples received by individual sample tray (360).

Each sidewall (366) is spaced from the adjacent sidewall by a predetermined width. This with is generally configured to correspond to about the width of a single tissue sample. In some examples, this width can be two times the diameter of cutter (130) or less. In other examples, the width between each sidewall (366) is approximately equivalent to the diameter of the cutter (130).

To communicate vacuum to tissue sample chamber (376), floor (368) further includes a plurality of vacuum openings (374) that communicate between tissue sample chamber (376) and the exterior of individual sample tray (360). As will be described in greater detail below, individual sample tray (360) is configured to pull a tissue sample though cutter (130) and into tissue sample chamber (376) when vacuum is applied though vacuum openings (374) and into tissue sample chamber (376).

Handle portion (380) protrudes proximally from tray portion (362). Handle portion (380) is configured to permit an operator to manipulate individual sample tray (360) to move individual sample tray (360) relative to rotatable member (330). In particular, handle portion (380) includes a generally rectangular shaped grasping feature (382) that is configured for grasping by an operator. Although not shown, it should be understood that grasping feature (382) can include features to enhance an operator's grip when gripping grasping feature (382).

Seal (390) is disposed between tray portion (362) and handle portion (380). Seal (390) extends outwardly from the oval shaped exterior of tray portion (362) to seal against proximal wall (338) of rotatable member (330). As will be described in greater detail below, seal (390) is generally configured to promote the flow of vacuum from vacuum port (314) of outer cup (310), though vacuum openings (374) in floor (368) of tray portion (362) and out of tray portion (362) to cutter (130). Seal (390) of the present example is shown as an o-ring. However, in other examples it should be understood that seal (390) may take on numerous alternative forms such as a wiper seal. Alternatively, in still other examples, seal (390) can be omitted entirely and be replaced with a sealing interference fit between tray portion (362) and proximal wall (338) of rotatable member (330).

Figure 10:
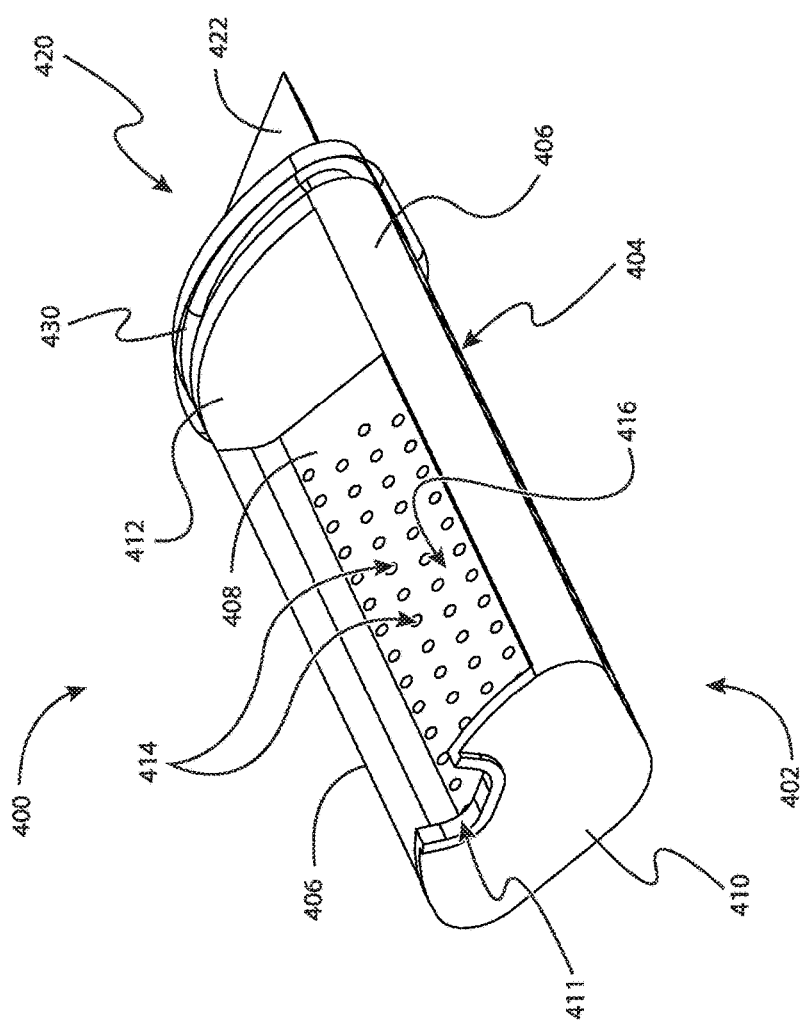
FIG. 10 depicts a perspective view of a bulk sample tray of the tissue sample holder of FIG. 2.
Figure 11:
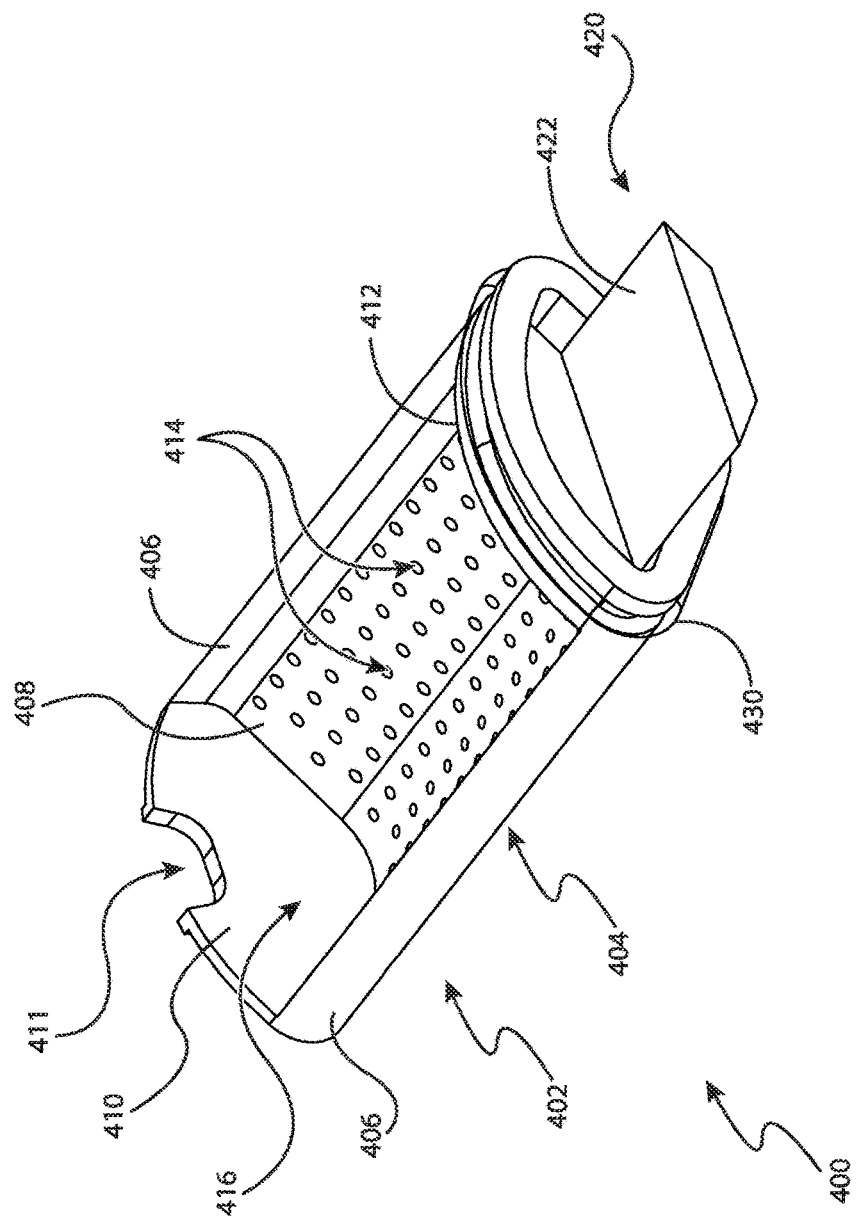
FIG. 11 depicts another perspective view of the bulk sample tray of FIG. 10.

FIGS. 10 and 11 show bulk sample tray (400) in greater detail. As will be understood, bulk sample tray (400) is generally configured to receive a plurality of tissue samples therein. Bulk sample tray (400) comprises a tray portion (402), a handle portion (420), and a seal (430) disposed between tray portion (402) and handle portion (420). Tray portion (402) includes a strip (404) that defines a generally pie-shaped external cross-section that corresponds to the pie shape of each bulk tray opening (342) of rotatable member (330). Strip (404) further defines a front wall (410), a pair of sidewalls (406), a floor (408), and a back wall (412). Sidewalls (406), floor (408), front wall (410), and back wall (412) generally define a bulk tissue sample chamber (416) that is configured to receive a plurality of tissue samples though a tissue opening (411) in front wall (410).

To communicate vacuum to tissue sample chamber (416), floor (408) further includes a plurality of vacuum openings (414) that communicate between tissue sample chamber (416) and the exterior of bulk sample tray (400). As will be described in greater detail below, bulk sample tray (400) is configured to pull tissue samples though cutter (130) and into tissue sample chamber (416) when vacuum is applied though vacuum openings (414) and into tissue sample chamber (416).

To accommodate a greater number of tissue samples, floor (408) generally defines a V-shaped transverse cross-section with the legs of the "V" extending upwardly to sidewalls (406). This V-shape of floor (408) increases the volume of tissue sample chamber (416) to accommodate more tissue samples. Additionally, to promote the flow of vacuum as tissue sample chamber (416) is filled, vacuum openings (414) are spaced evenly across the entirety of floor (408).

In addition to floor (408) being V-shaped, each side wall (406) curves outwardly from tissue sample chamber (416). The curvature of side walls (406) generally increases the volume of tissue sample chamber (416). In addition, the curvature of side walls (406) corresponds to the curvature of each radiused surface (335) defined by each tray protrusion (334) of rotatable member (330). This correspondence between the shape of side walls (406) and the shape of radiused surfaces (335) permits tray protrusions (334) to grip side walls (406) to thereby hold bulk sample tray (400) in position within rotatable member (330).

Handle portion (420) protrudes proximally from tray portion (402). Handle portion (420) is configured to permit an operator to manipulate bulk sample tray (400) to move bulk sample tray (400) relative to rotatable member (330). In particular, handle portion (420) includes a generally trapezoidal shaped grasping feature (422) that is configured for grasping by an operator. Although not shown, it should be understood that grasping feature (422) can include features to enhance an operator's grip when gripping grasping feature (422).

Seal (430) is disposed between tray portion (402) and handle portion (420). Seal (430) extends outwardly from the oval shaped exterior of tray portion (402) to seal against proximal wall (338) of rotatable member (330). As will be described in greater detail below, seal (430) is generally configured to promote the flow of vacuum from vacuum port (314) of outer cup (310), though vacuum openings (414) in floor (408) of tray portion (402) and out of tray portion (402) to cutter (130). Seal (430) of the present example is shown as an O-ring. However, in other examples it should be understood that seal (430) may take on numerous alternative forms such as a wiper seal. Alternatively, in still other examples, seal (430) can be omitted entirely and be replaced with a sealing interference fit between tray portion (402) and proximal wall (338) of rotatable member (330).

FIGS. 12-16 show an exemplary use of tissue sample holder (300) to collect tissue samples from biopsy device (10). As will be described in greater detail below, tissue sample holder (300) is generally configured to rotate rotatable member (330) via manual rotation wheel (350) to selectively index individual sample tray (360) or any one of bulk sample trays (400) with cutter (130) to collect tissue samples. Such selectable indexing of tissue sample holder (300) provides selective transitioning of tissue sample holder (300) between an individual sample collection mode and a bulk sample collection mode. When in the individual sample collection mode, tissue sample holder (300) can provide an operator more flexibility with respect to tissue sample analysis. When in the bulk sample collection mode, tissue sample holder (300) can provide an operator with the ability to collect a relatively large number of tissue samples without having to replace or otherwise empty trays (400). Although various methods of using these two modes in connection with a biopsy procedure are described herein, it should be understood that numerous other methods may be used as will be apparent to those of ordinary skill in the art in view of the teachings herein.

Figure 12:
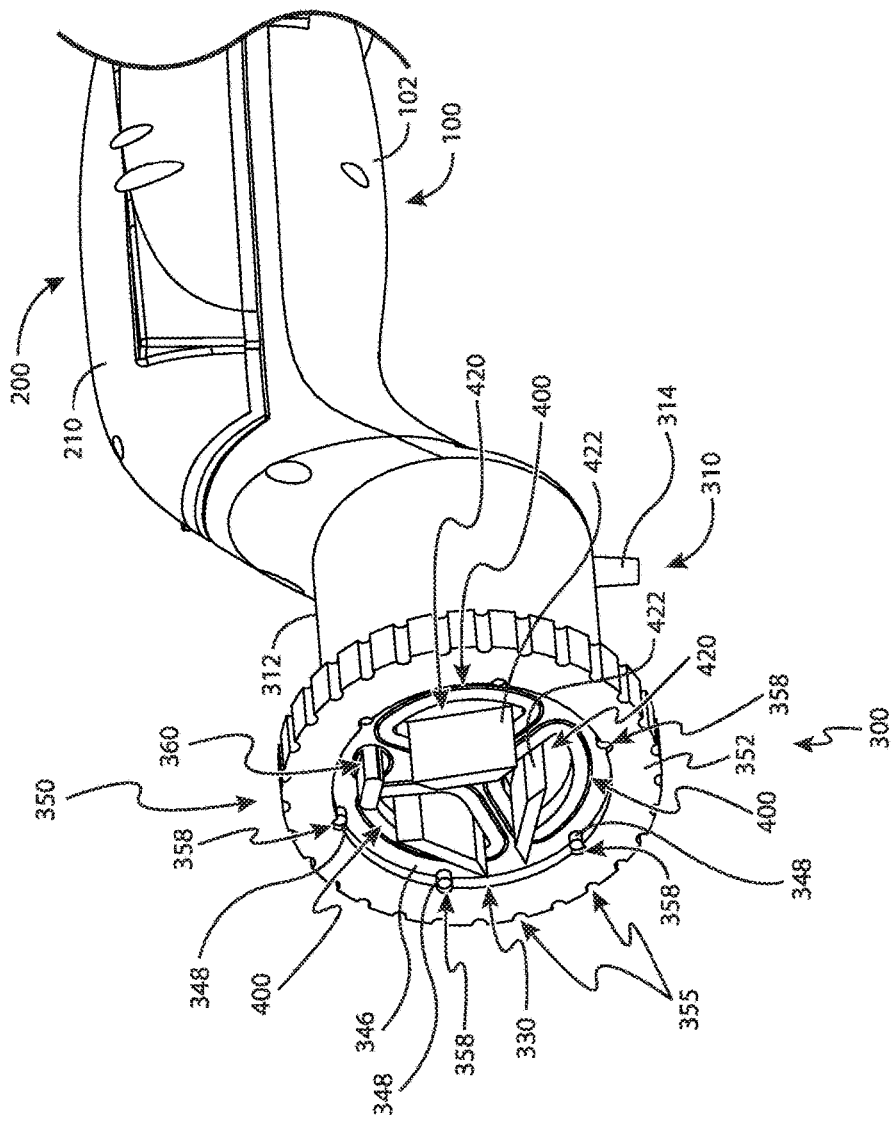
FIG. 12 depicts another perspective view of the tissue sample holder of FIG. 2, with the individual sample tray of FIG. 9 indexed with a cutter.

In one merely exemplary use, an operator may begin a biopsy procedure with tissue sample holder (300) in the individual sample collection mode as shown in FIG. 12. In some uses, tissue sample holder (300) is transitioned to the individual sample collection mode prior to beginning the biopsy procedure. Alternatively, tissue sample holder (300) is set to the individual sample collection mode after placement of needle (110) within a patient, but prior to initiation of tissue sample collection via cutter (130). In either case, it should be understood that in the present mode of operation, tissue sample holder (300) is set to the individual sample collection mode so that a first sample acquired by cutter (130) is transported into individual sample tray (360) rather than any one of bulk trays (400). In this method of use, an operator may be permitted to analyze the first sample to verify a desired positioning of needle (110) within a patient or otherwise conduct some preliminary analysis of the first tissue sample.

In the present use example, tissue sample holder (300) is transitioned to the individual sample collection mode by an operator grasping manual rotation wheel (350) and rotating manual rotation wheel (350) in a clockwise or counter clockwise direction. Manual rotation wheel (350) is rotated by an operator in a desired clockwise or counter clockwise direction to rotate rotatable member (330). This rotation of rotatable member (330) results in corresponding rotation of sample trays (360, 400), which are disposed within rotatable member (330). Rotation of rotatable member (330) continues until individual sample tray (360) is positioned in a "twelve o'clock" position, corresponding to the position shown in FIG. 12. In this position, individual sample tray (360) is aligned with cutter (130) such that tissue samples received by tissue sample holder (300) from cutter (130) are received within individual sample tray (360).

Once tissue sample holder (300) is transitioned to the individual sample collection mode as shown in FIG. 12, the first tissue sample may be acquired by actuating cutter (130) relative to cannula (113) to sever the first tissue sample. Vacuum is next applied to vacuum port (314) of outer cup (310). This application of vacuum induces a negative pressure within the interior of rotatable member (330). This negative pressure flows into tissue sample chamber (376) of individual sample tray (360) via vacuum openings (374) in floor (368) of individual sample tray (360). Vacuum then flows from tissue sample chamber (376) of individual sample tray (360) to cutter (130) to thereby transport the first tissue sample proximally though cutter and into tissue sample chamber (376) of individual sample tray (360). Venting may be applied to the distal face of the tissue sample within cutter (130) to thereby provide a pressure differential that results in proximal translation of the tissue sample through cutter (130) into tissue sample chamber (376).

Figure 13:
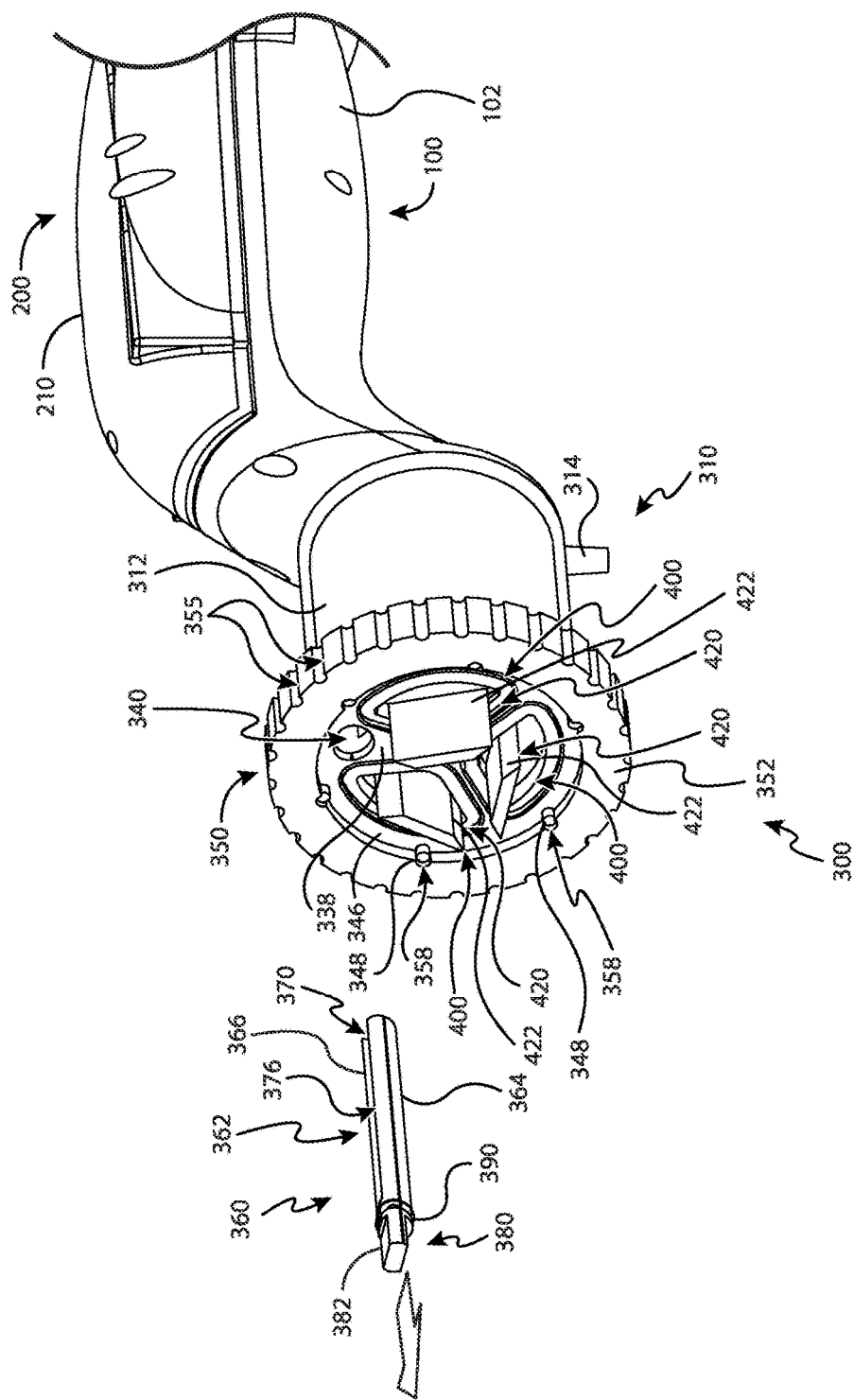
FIG. 13 depicts still another perspective view of the tissue sample holder of FIG. 2, with the individual sample tray of FIG. 9 removed from the tissue sample holder.

Once the first tissue sample is received within individual sample tray (360), an operator may desire to inspect the first tissue sample. To inspect the first tissue sample, an operator grasps individual sample tray (360) via grasping feature (382) to pull individual sample tray (360) proximally and out of rotatable member (330), as shown in FIG. 13. Once individual sample tray (360) is removed from rotatable member (330), the first tissue sample can be visually inspected. If an operator desires to touch, feel, or otherwise manipulate the first tissue sample, an operator may remove the first tissue sample from individual sample tray (360). In addition, or in the alternative, if an operator desires analysis beyond visual inspection, the first tissue sample can be removed from individual sample tray (360) and placed in another container for specimen radiograph or any other suitable preliminary tissue sample analysis modality.

Once preliminary analysis of the first tissue sample is complete, in some instances an operator may not be satisfied with the first tissue sample. For instance, as described above, the first tissue sample may be used to assess the positioning of needle (110) within a patient. If preliminary analysis of the first tissue sample indicates that the positioning of needle (110) within a patent is undesirable, an operator may desire to reposition needle (110) and acquire another sample for inspection. In this case, an operator may discard the first tissue sample, insert individual sample tray (360) back into rotatable member (330), and then repeat the steps described above to acquire a second tissue sample for preliminary analysis. This process may be repeated as many times as necessary until an operator is satisfied with a tissue sample collected within individual sample tray (360).

Figure 14:
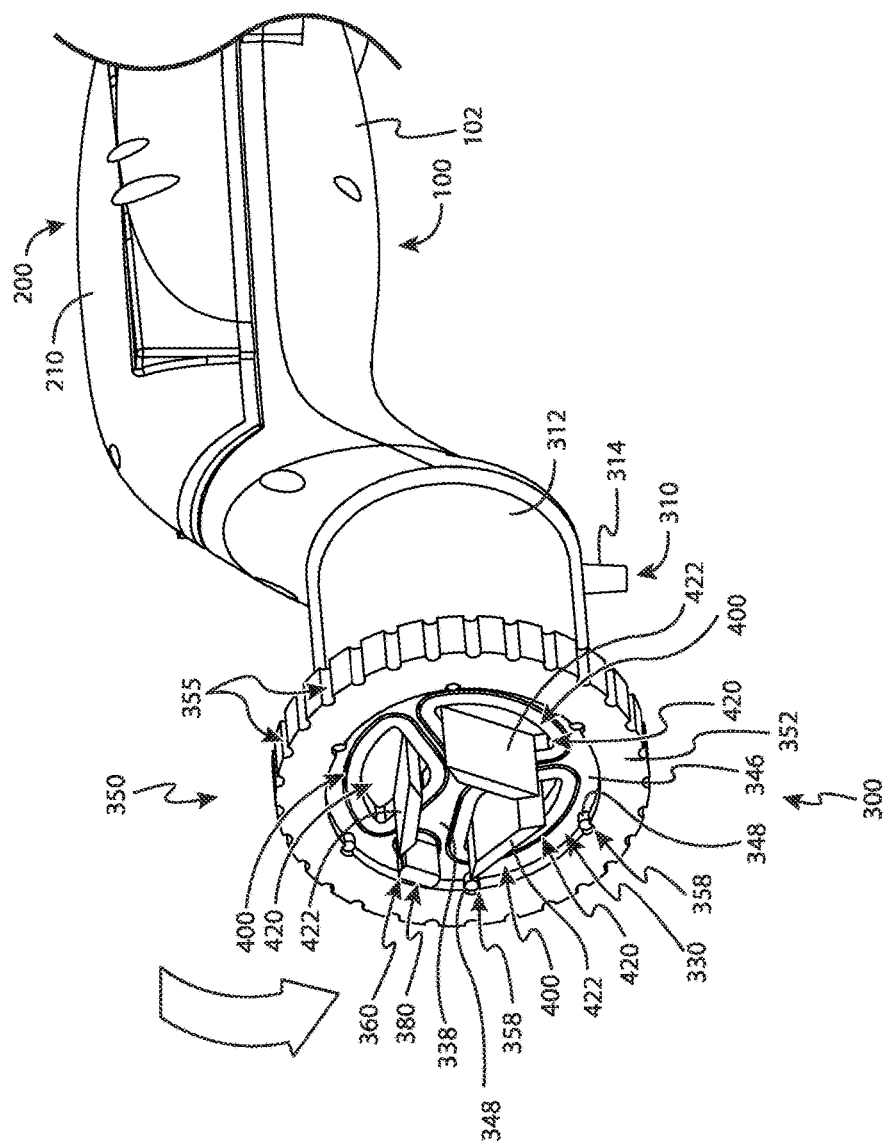
FIG. 14 depicts yet another perspective view of the tissue sample holder of FIG. 2, with the bulk sample tray of FIG. 10 indexed with the cutter.

Once an operator is satisfied with the first tissue sample, or any other subsequent sample acquired with individual sample tray (360) thereafter, an operator may next desire to acquire tissue samples in the bulk sample collection mode. To transition tissue sample holder (300) to the bulk collection mode, an operator grasps manual rotation wheel (350) to rotate rotatable member (330) via manual rotation wheel (350) in a clockwise or counter clockwise direction. Rotation continues until any one of bulk sample trays (400) are positioned in the twelve o'clock position as shown in FIG. 14. In the position shown in FIG. 14, a selected bulk sample tray (400) is indexed with cutter (130) to receive tissue samples therein when severed by cutter (130).

Once rotatable member (330) of tissue sample holder (300) is rotated to index a selected bulk sample tray (400) with cutter, tissue sample holder (300) is transitioned to the bulk sample collection mode. In the bulk sample collection mode, an operator can collect a plurality of tissue samples within each bulk sample tray (400). For instance, tissue samples can be severed by actuating cutter (130) relative to cannula (113) of needle (110). Once each tissue sample is severed, vacuum is applied to tissue sample holder (300) via vacuum port (314) of outer cup (310). The vacuum applied to vacuum port (314) then flows into rotatable member (330), into tissue sample chamber (416) of the selected bulk sample tray (400), through tissue opening (411), and into cutter (130). This flow of vacuum creates a fluid circuit that transports each tissue sample severed by cutter (130) though cutter (130) and into tissue sample chamber (416) of the selected bulk sample tray (400). As noted above, venting may be applied to the distal face of the tissue sample within cutter (130) to thereby provide a pressure differential that results in proximal translation of the tissue sample through cutter (130) into tissue sample chamber (416).

Tissue samples can be continued to be collected until the selected bulk sample tray (400) reaches its sample capacity. Although the particular sample capacity may vary by a number of factors such as the particular dimensions of tissue sample holder (300) or the gauge of needle (110), in some examples each bulk sample tray (400) can receive anywhere between 10-20 tissue samples.

Figure 15:
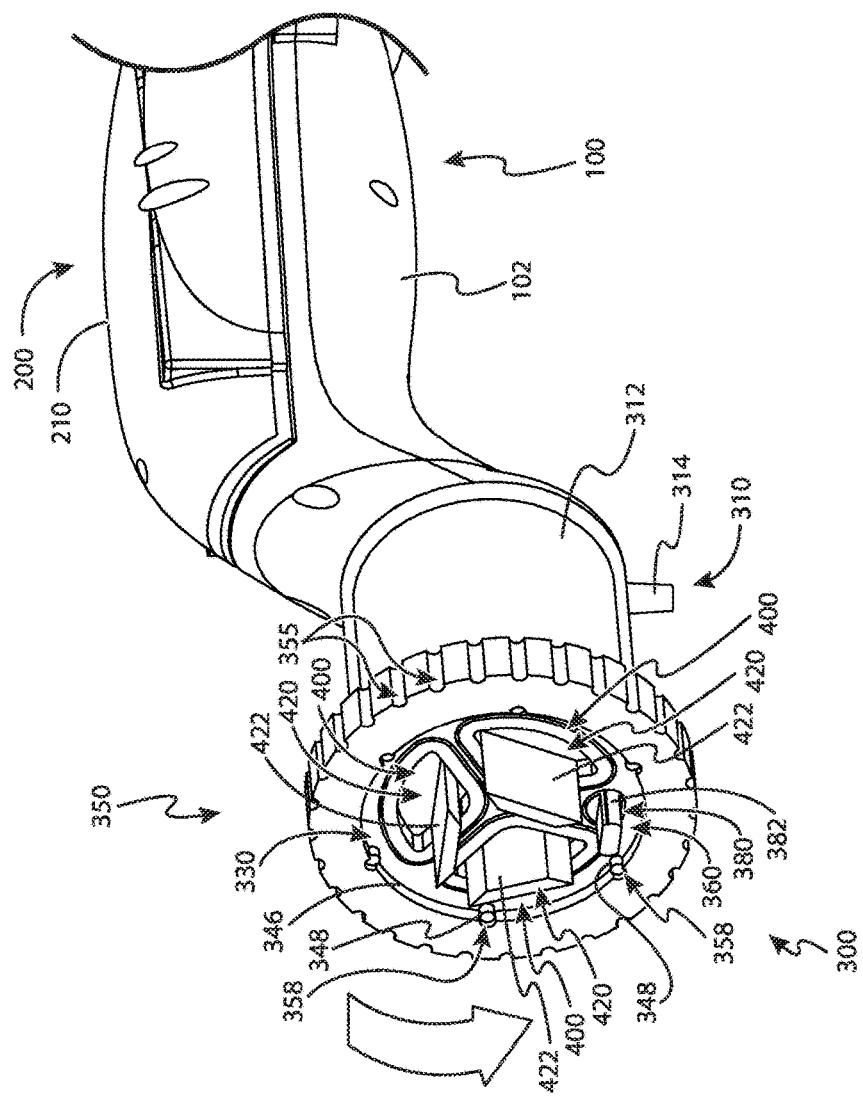
FIG. 15 depicts yet another perspective view of the tissue sample holder of FIG. 2, with another bulk sample tray of FIG. 10 indexed with the cutter.

Regardless of the particular capacity of each bulk sample tray (400), once the selected bulk sample tray (400) is full, an operator may continue collecting tissue samples in the bulk collection mode by grasping manual rotation wheel (350) and rotating rotatable member (330) via manual rotation wheel (350) to index another bulk sample tray (400) with cutter (130) as shown in FIG. 15. Tissue sample collection may continue until two of the three bulk sample trays (400) are filled to capacity.

Figure 16:
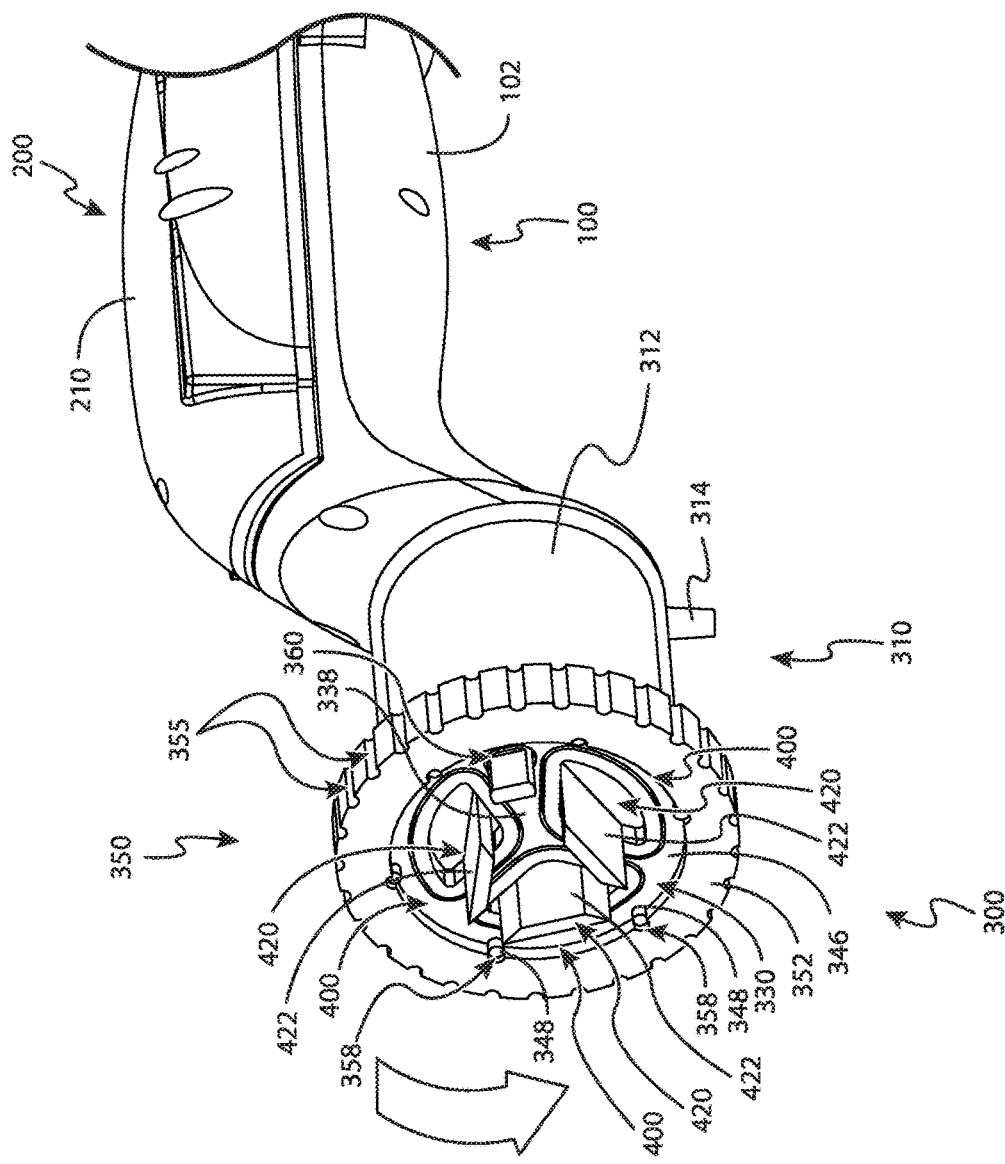
FIG. 16 depicts yet another perspective view of the tissue sample holder of FIG. 2, with another bulk sample tray of FIG. 10 indexed with the cutter.

Once two of the three bulk sample trays (400) are filled to capacity, an operator can continue collecting samples in the bulk collection mode by rotating tissue sample holder (300) as described above to position tissue sample holder (300) as shown in FIG. 16. This positions the third and final bulk sample tray (400) into communication with cutter (130) to receive severed tissue samples as they are severed by cutter (130). Bulk tissue sample collection can continue until all three bulk sample trays (400) are filled.

Once all bulk sample trays (400) are filled, an operator can simply finalize the biopsy procedure by removing needle (110) from a patient and performing other finalizing steps. Alternatively, in some uses an operator may desire to conduct further tissue sample analysis. For instance, in some uses, an operator may desire to analyze one or more tissue samples to determine if an entire lesion was removed during bulk collection. To engage in further analysis, an operator can return tissue sample holder (300) to the individual collection mode described above by rotating tissue sample holder (300) to the position shown in FIG. 12. Once in the individual sample mode, an operator may collect a tissue sample and conduct a visual analysis or other form of analysis as described above by removing individual sample tray (360) from rotatable member (330). This process of individual tissue sample analysis may then be repeated until an operator obtains satisfactory results.

If an operator desires to collect additional bulk samples after analysis of one or more individual samples, the operator may transition tissue sample holder (300) back to bulk collection mode as described above. If all bulk sample trays (400) are full at this stage, an operator may remove one or more bulk sample trays (400) to empty the one or more bulk sample trays (400). Bulk tissue collection may then continue until a desired number of tissue samples have been collected.

Although not described above, it should be understood that at any time during bulk sample collection an operator may selectively switch between bulk sample collection mode and individual sample collection mode. This may be desirable to engage in intermediate procedure individual sample analysis via individual sample collection mode. For instance, in some uses an operator may use bulk sample collection mode to remove an entire lesion from a patient. Thus, it may be desirable to periodically check progress toward this end using individual sample collection mode. In such a use, if a visual inspection via individual collection mode indicates suspect tissue, an operator may return to bulk sample collection mode to collect additional samples. However, if a visual inspection via individual collection mode indicates no suspect tissue, an operator may conclude that adequate samples have been taken and the procedure may be finalized.

III. EXEMPLARY ALTERNATIVE TISSUE SAMPLE HOLDER

Figure 17:
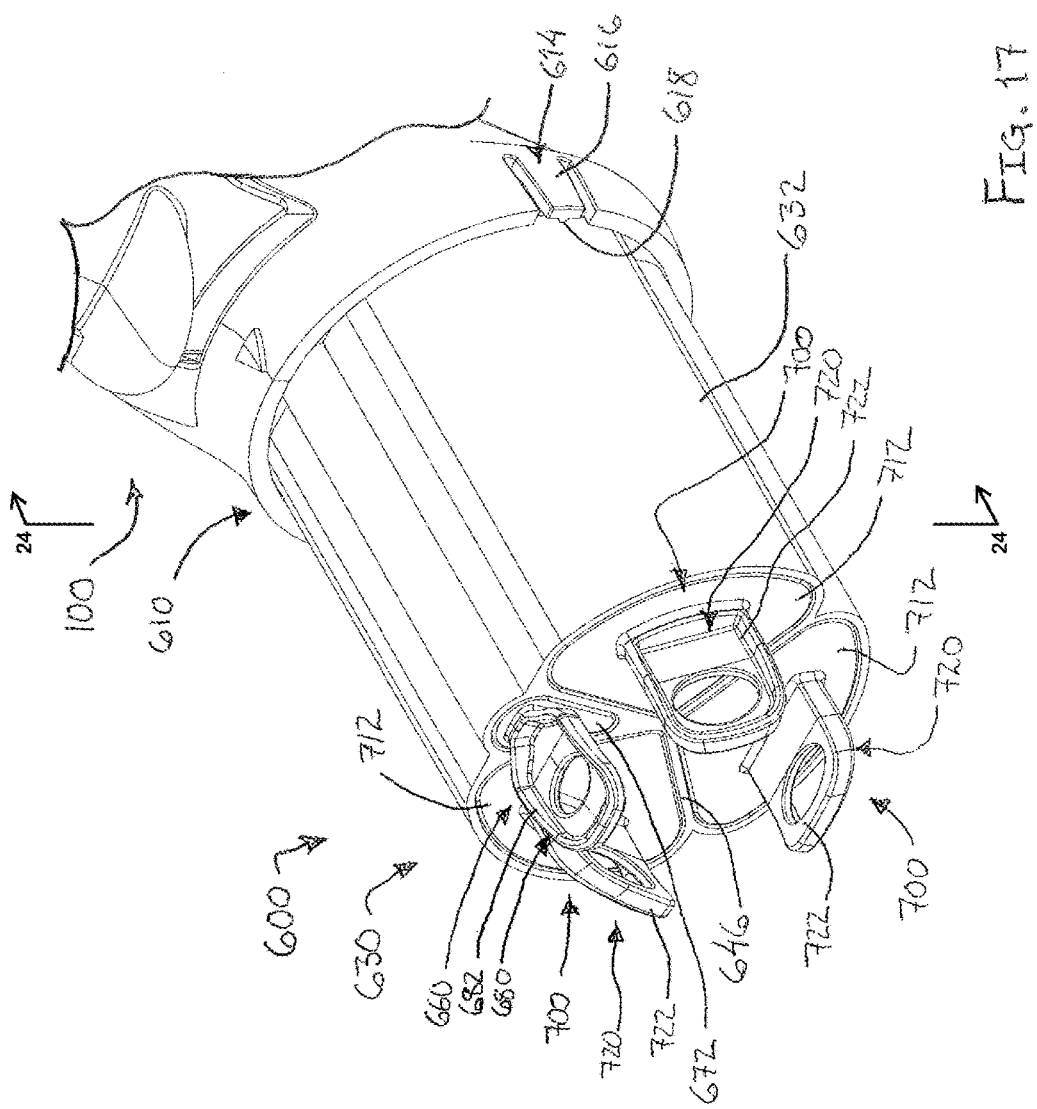
FIG. 17 depicts a perspective view of an exemplary alternative tissue sample holder for use with the biopsy device of FIG. 1.
Figure 18:
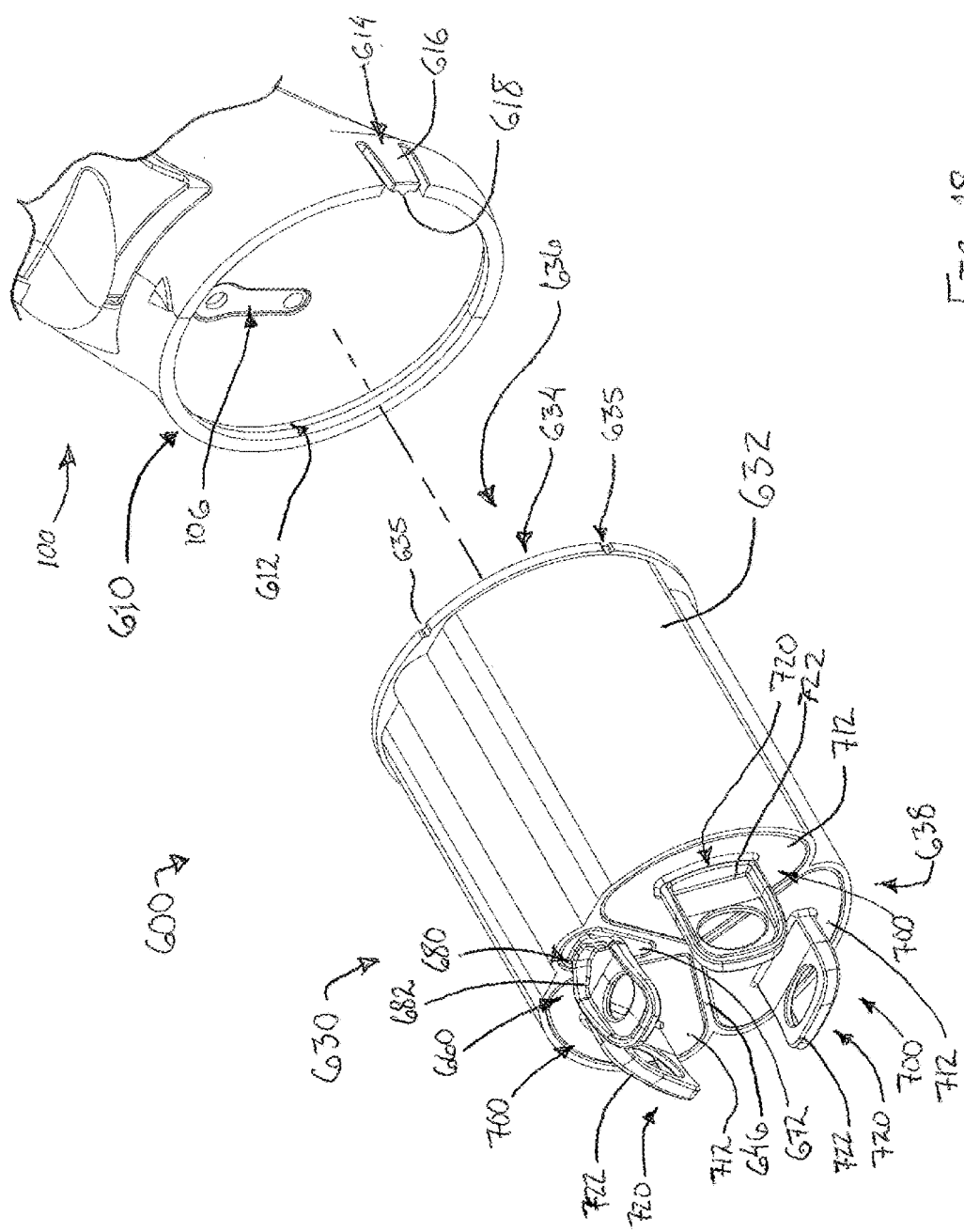
FIG. 18 depicts perspective view of the tissue sample holder of FIG. 17, with the tissue sample holder decoupled from a probe of the biopsy device of FIG. 1.
Figure 19:
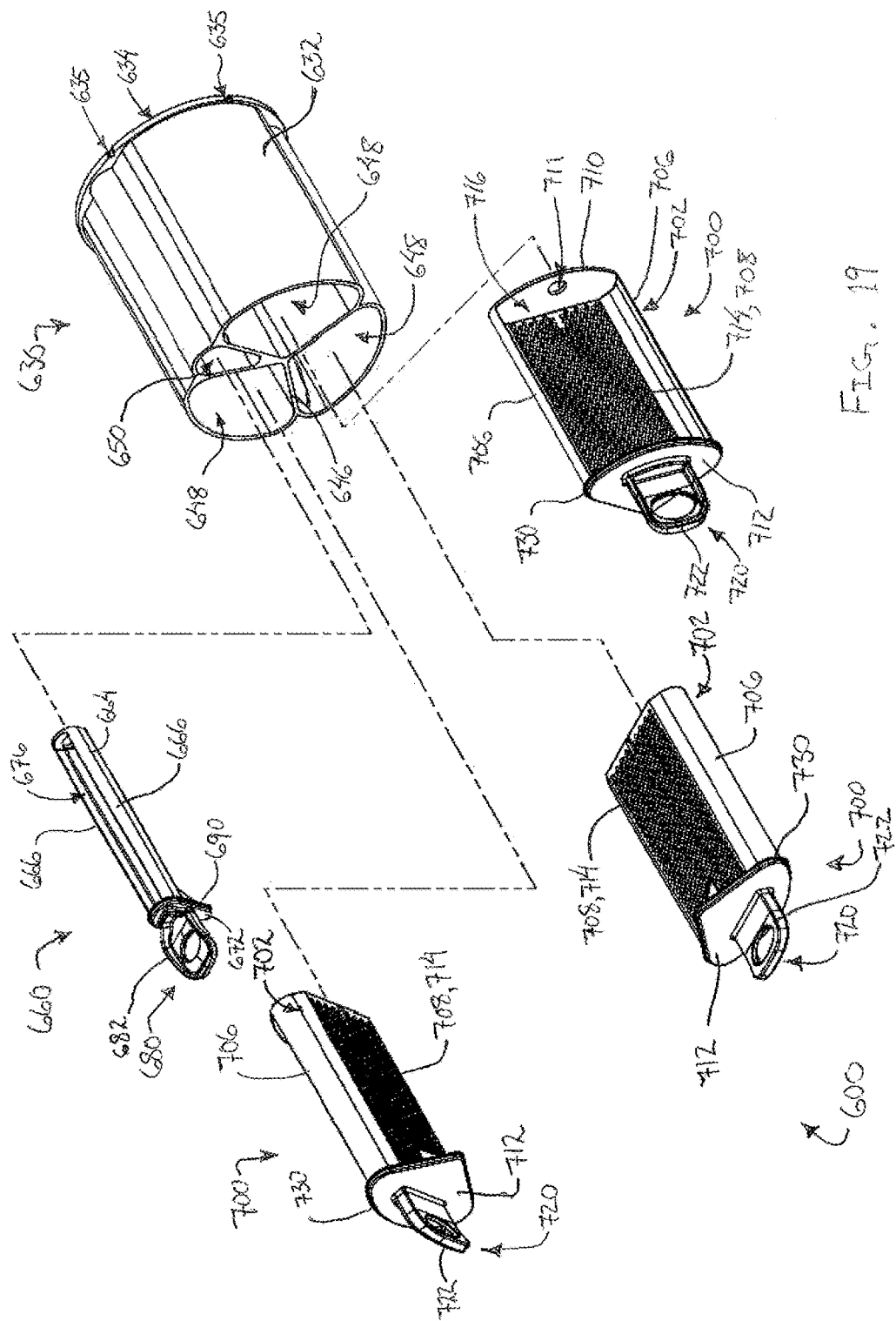
FIG. 19 depicts a perspective exploded view of the tissue sample holder of FIG. 17.

FIG. 17 depicts an exemplary alternative tissue sample holder (600) that can be used with biopsy device (10) in lieu of tissue sample holder (300) described above. Like with tissue sample holder (300) described above, tissue sample holder (600) of the present example includes a rotatable member (630), an individual sample tray (660), and three bulk sample trays (700). Unlike tissue sample holder (300) described above, tissue sample holder (600) of the present example omits structures similar to outer cup (310). Instead, tissue sample holder (600) is coupled directly to probe (100). As will be described in greater detail below, to facilitate this configuration, probe (100) may include certain coupling features (610) that facilitate coupling between rotatable member (630) and probe (100). For instance, in the present example the proximal end of probe (100) includes a coupler (610) defining a cylindrical proximal channel (612). As will be described in greater detail below, this proximal channel (612) is configured to receive at least a portion of rotatable member (630) to permit rotation of rotatable member (630) relative to probe (100), while also fixing the axial position of rotatable member (630) relative to probe (100).

It should be understood that in other examples coupling between probe (100) and rotatable member (630) can be accomplished in a variety of ways. For instance, in some examples tissue sample holder (600) can include a shortened version of a structure similar to outer cup (310). In this configuration, the shortened version of the structure similar to outer cup (310) can facilitate coupling between an unmodified probe (100) and rotatable member (630), while still maintaining unobstructed access to rotatable member (630). As will be understood, this unobstructed access to rotatable member (630) is generally desirable to promote manual rotation of tissue sample holder (600) by actuating rotatable member (630) directly rather than indirectly through a structure similar to manual rotation wheel (350).

Probe (100) can also be modified to include an indexer (614) incorporated into coupler (610). In the present example, indexer (614) includes a resilient portion (616) and an indexing tooth (618). Resilient portion (616) is generally configured to bias indexing tooth (618) into a portion of rotatable member (630). As will be described in greater detail below, indexer (614) is generally configured to resiliently engage at least a portion of rotatable member (630) to resiliently bias rotatable member (630) towards a plurality of indexing positions.

Figure 20:
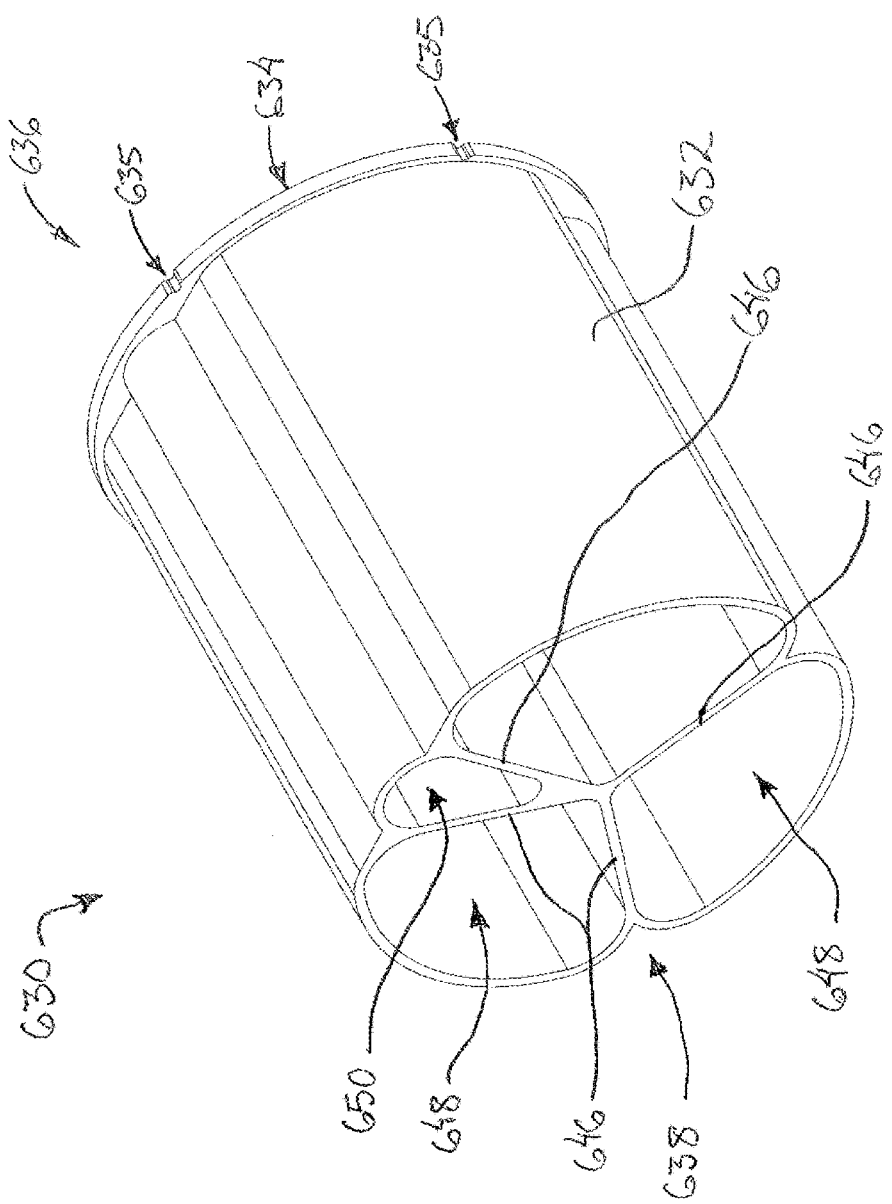
FIG. 20 depicts a perspective view of a rotatable member of the tissue sample holder of FIG. 17.
Figure 21:
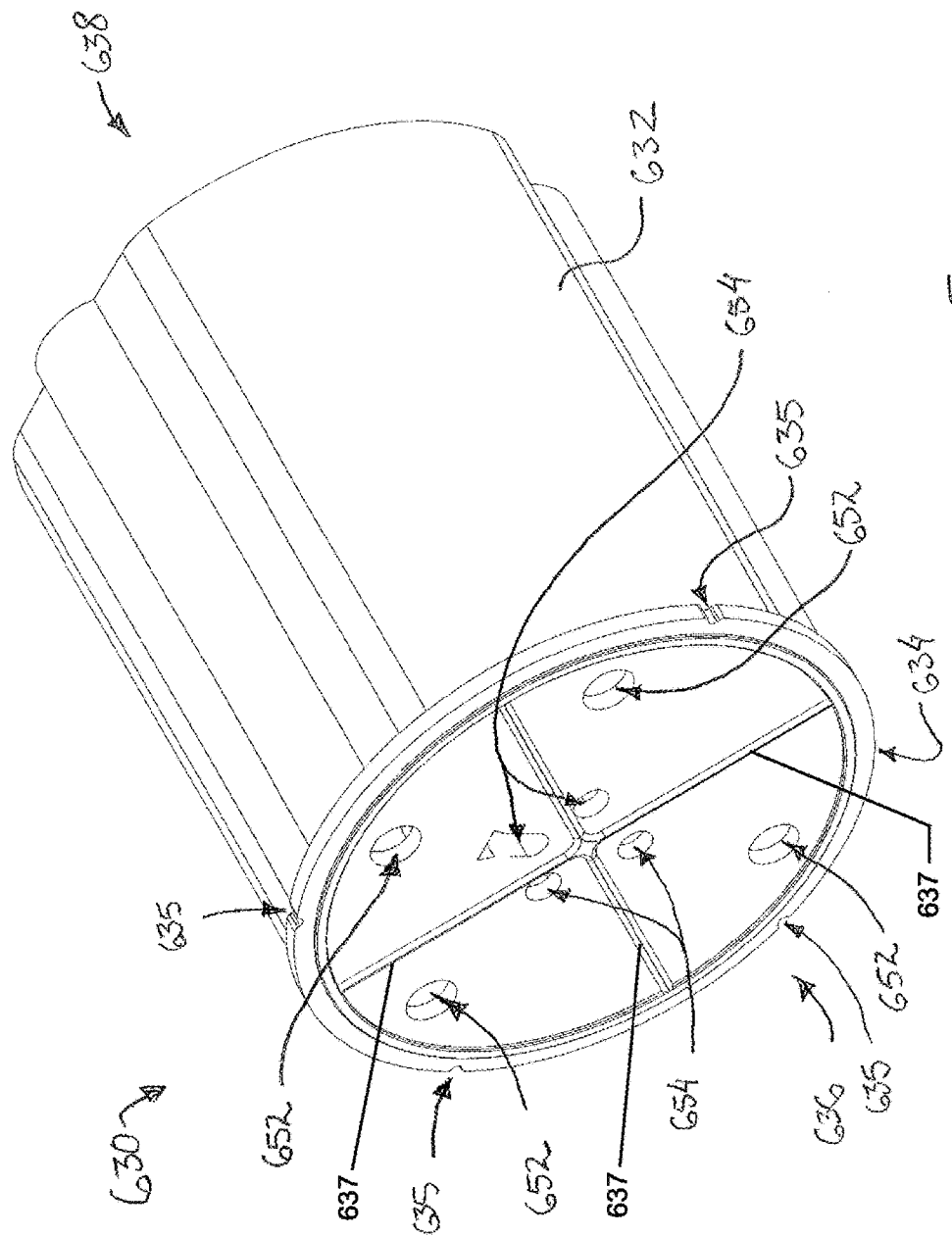
FIG. 21 depicts another perspective view of a rotatable member of the tissue sample holder of FIG. 17.

FIGS. 20 and 21 show rotatable member (630) in greater detail. As can be seen, rotatable member (630) comprises an outer wall (632) extending between a distal end (636) and a proximal end (638). Outer wall (632) defines a generally cylindrical, but irregular cross-section. As will be described in greater detail below, outer wall (632) at least partially defines a plurality of chambers (648, 650) for receiving one or more trays (660, 700). To accommodate each tray (660, 700), outer wall (632) generally mirrors the shape of each tray (660, 700). Thus, although outer wall (632) defines a generally cylindrical shape, this general shape is interrupted by inwardly extending and outwardly extending curvatures corresponding to the shape of each tray (660, 700). This configuration is generally desirable to increase the usable volume within rotatable member (630). In addition, this configuration also provides a relatively irregular exterior surface of rotatable member (630) that can be used to enhance an operator's grip on rotatable member (630) to thereby provide manual rotation of rotatable member (630) via outer wall (632).

The interior of outer wall (632) includes a plurality of tray walls (646) extending from distal end (636) to proximal end (638). Each wall (646) also extends radially inwardly into the interior space defined by outer wall (632) until converging with the other tray walls (646). Thus, tray walls (646) together define a plurality of discrete tray chambers (648, 650). In the present example, tray walls (646) collectively define three bulk tray chambers (648) and one individual tray chamber (650). However, it should be understood that in other examples various alternative configurations can be used such as a plurality of bulk tray chambers (648) and a plurality of individual tray chambers (650), one bulk tray chamber (648) and a plurality of individual tray chambers (650), or some alternative combination thereof.

Each tray wall (646) is angularly spaced around the interior circumference of outer wall (632). The angular spacing of each tray wall (646) relative to adjacent tray walls (646) corresponds to a width of either individual sample tray (660) or bulk sample tray (700). Due to this spacing, tray chambers (648, 650) defined by tray walls (646) are generally triangular or pie-shaped. In addition, each tray wall (646) is integrated into outer wall (632). In the present configuration, each tray wall (646) is integrated into outer wall (632) at a trough or indentation defined by outer wall (632).

As best seen in FIG. 20, proximal end (638) is generally open to expose tray chambers (648, 650) and tray walls (646) relative to the exterior of rotatable member (630). Accordingly, it should be understood that each tray chamber (648, 650) is configured to receive a corresponding tray (660, 700) directly via proximal end (638). Although proximal end (638) is generally open in the present example, it should be understood that in other examples proximal end (638) can include a wall or other structural features to close proximal end (638) relative to the exterior of rotatable member (630). In such a configuration, the wall may include openings to facilitate entry of trays (660, 700) into tray chambers (648, 650) of rotatable member (630).

As best seen in FIG. 21, distal end (636) of rotatable member (630) defines a generally closed end. To facilitate communication of vacuum and tissue samples from probe (100) into tray chambers (648, 650), distal end (636) defines a plurality of sample openings (652) and a plurality of vacuum openings (654). Each sample opening (652) is positioned to correspond to a particular tray chamber (648, 650) to facilitate communication of a tissue sample from probe (100) and into a tray (660, 700) indexed with cutter (130) of probe (100). Vacuum is supplied from probe (100) into an indexed tray chamber (648, 650) via a corresponding vacuum opening (654). As will be described in greater detail below, vacuum supplied to the indexed tray chamber (648, 650) is generally used to transport a severed tissue sample through cutter (130) and into the indexed tray (660, 700).

In the present example, the vacuum opening (654) associated with individual tray chamber (650) can be shaped differently relative to the vacuum openings (654) associated with bulk tray chambers (648). This configuration is generally desirable to promote the free flow of vacuum through the vacuum opening (654) associated with individual tray chamber (650). For instance, as described above, individual tray chamber (650) is generally smaller relative to bulk tray chambers (648). Due to this reduced size, tray (646) converge to form individual tray chamber (650) at a sharper angle relative to the tray walls (646) that form bulk tray chambers (648). Because of this, if the vacuum opening (654) associated with individual tray chamber (650) was identical to the vacuum openings (654) associated with bulk tray chambers (648), tray walls (646) might obstruct at least a portion of the vacuum opening (654) associated with individual tray chamber (650). To avoid any such obstruction, the vacuum opening (654) associated with individual tray chamber (650) can include a partial rectangular extension extending upwardly. In addition, it should be understood that tray walls (646) can include some modification at the interface between the vacuum opening (654) associated with individual tray chamber (650) and tray walls (646). In the present example, this includes a step-up from a portion of the vacuum opening (654) associated with individual tray chamber (650) and tray walls (646). In other examples, tray walls (646) may be equipped with a channel adjacent to the vacuum opening (654) associated with individual tray chamber (650). Alternatively, tray walls (646) may protrude outwardly at the interface between the vacuum opening (654) associated with individual tray chamber (650) and tray walls (646). Such an outward protrusion may generally match a diameter of the vacuum opening (654) associated with individual tray chamber (650). Of course, numerous alternative configurations may be used as will be apparent to those of ordinary skill in the art in view of the teachings herein.

Between each set of openings (652, 654) corresponding to each chamber (648, 650), distal end (636) defines a plurality of ribs (637). Ribs (637) extend inwardly from the exterior of rotatable member (630) and converging at the center of rotatable member (630), thereby forming an x-shaped pattern on distal end (636). Each rib (637) generally protrudes outwardly from the distal face of distal end (636). As will be understood, each rib (637) is configured to engage the proximal end of probe (100). In some examples the proximal end of probe (100) includes a rubber seal or gasket that engages directly with each rib (637). Thus, engagement between ribs (637) and the proximal end of probe (100) can provide a seal therebetween. This configuration generally provides fluid isolation between each sample opening (652) relative to the other sample openings (652); and fluid isolation between each vacuum opening (654) relative to the other vacuum openings (654). As will be understood, this fluid isolation generally promotes the flow of vacuum through only a single bulk tray chamber (648) and individual tray chamber (650) when said chamber (648, 650) is indexed with cutter (130) of probe (100).

Distal end (636) of rotatable member (630) further includes a distal flange (634). Distal flange (634) is generally configured to be received by probe to axially secure rotatable member (630) to probe (100), while permitting rotatable member (630) to rotate relative to probe (100). Distal flange (634) defines a plurality of indentations (635) spaced angularly around the exterior of distal flange (634). Each indentation (635) defines a generally triangular shape that corresponds to the triangular shape of indexing tooth (618) of indexer (614) described above. Additionally, each indentation (635) corresponds to a particular tray chamber (648, 650) defined by rotatable member (630). As will be described in greater detail below, this permits each indentation (635) to successively engage with indexing tooth (618) of indexer (614) to resiliently bias rotatable member (630) towards a plurality of indexing positions. Although each indentation (635) and indexing tooth (618) are shown as having corresponding generally triangular shapes in the present example, it should be understood that in other examples a plurality of alternative shapes can be used such as rounded, semi-ovular, hemispherical, or etc.

Figure 22:
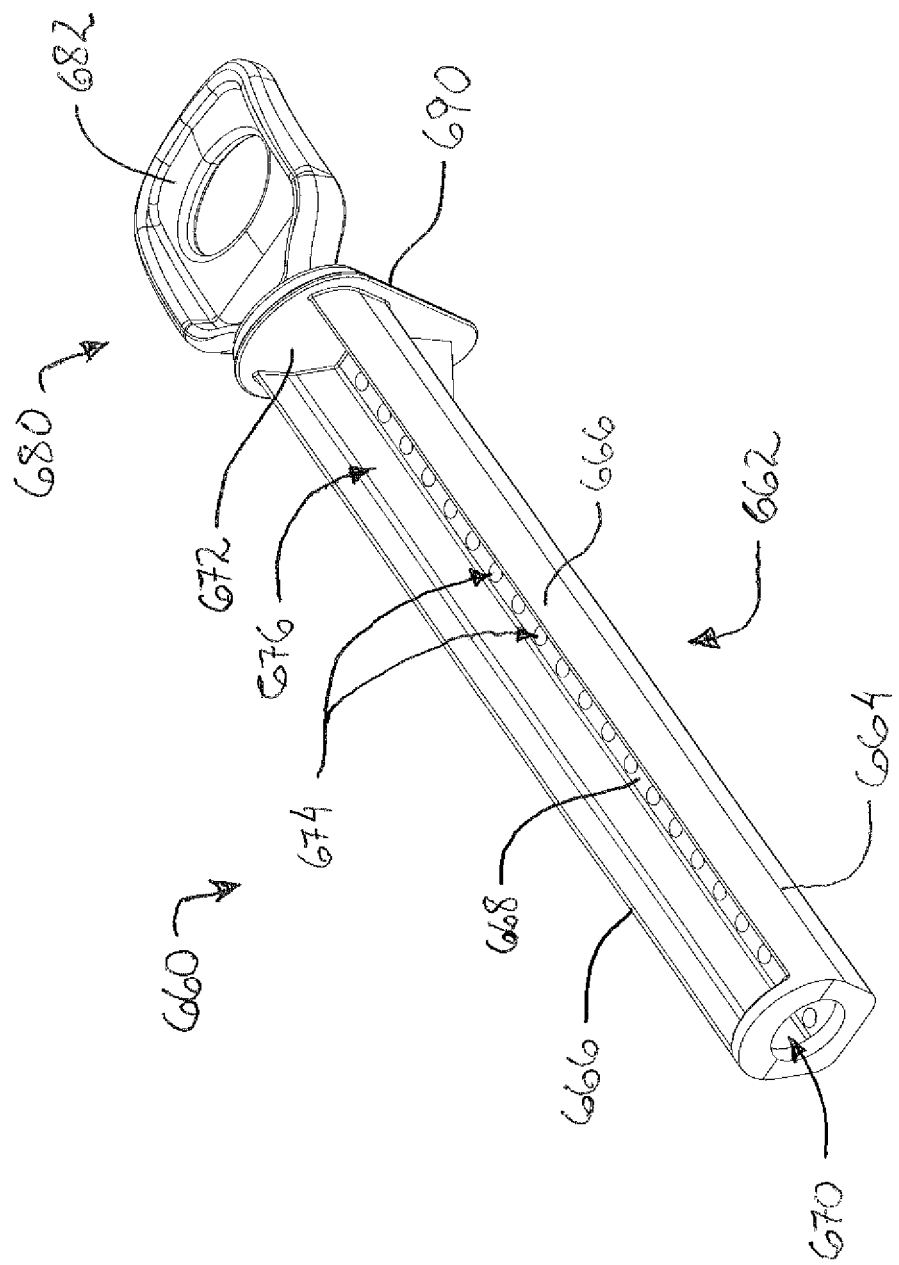
FIG. 22 depicts a perspective view of an individual sample tray of the tissue sample holder of FIG. 17.

FIG. 22 shows individual sample tray (660) in greater detail. As will be understood, individual sample tray (660) is generally configured to receive only one single tissue sample therein. Individual sample tray (660) comprises a tray portion (662), a handle portion (680), and a seal (690) disposed between tray portion (662) and handle portion (680). Tray portion (662) includes a strip (664) that defines a generally oval-shaped or egg-shaped cross-section that corresponds to at least a portion of the shape of individual tray chamber (650) of rotatable member (630). Strip (664) further defines a sample opening (670), a pair of sidewalls (666), a floor (668), and a back wall (672). Sidewalls (666), floor (668), and back wall (672) generally define a tissue sample chamber (676) that is configured to receive a single tissue sample though sample opening (670).

To communicate vacuum to tissue sample chamber (676), floor (668) further includes a plurality of vacuum openings (674) that communicate between tissue sample chamber (676) and the exterior of individual sample tray (660). As will be described in greater detail below, individual sample tray (660) is configured to pull a tissue sample though cutter (130) and into tissue sample chamber (676) when vacuum is applied though vacuum openings (674) and into tissue sample chamber (676).

Handle portion (680) protrudes proximally from tray portion (662). Handle portion (680) is configured to permit an operator to manipulate individual sample tray (660) to move individual sample tray (660) relative to rotatable member (630). In particular, handle portion (680) includes a generally rectangular shaped grasping feature (682) that is configured for grasping by an operator. Although not shown, it should be understood that grasping feature (682) can include features to enhance an operator's grip when gripping grasping feature (682).

Seal (690) is disposed between tray portion (662) and handle portion (680). Seal (690) extends outwardly from the oval-shaped exterior of tray portion (662) to seal against tray walls (646) and outer wall (632) of rotatable member (630). As will be described in greater detail below, seal (690) is generally configured to promote the flow of vacuum from a corresponding vacuum opening (654) of rotatable member (630), though vacuum openings (674) in floor (668) of tray portion (662) and out of tray portion (662) to cutter (130). Seal (690) of the present example is shown as a generally triangular flange that can be equipped with an o-ring or other sealing gasket. However, in other examples it should be understood that seal (690) may take on numerous alternative forms such as a wiper seal. Alternatively, in still other examples, seal (690) can be omitted entirely and be replaced with a sealing interference fit between tray portion (662) and walls (632, 646) of rotatable member (630).

Figure 23:
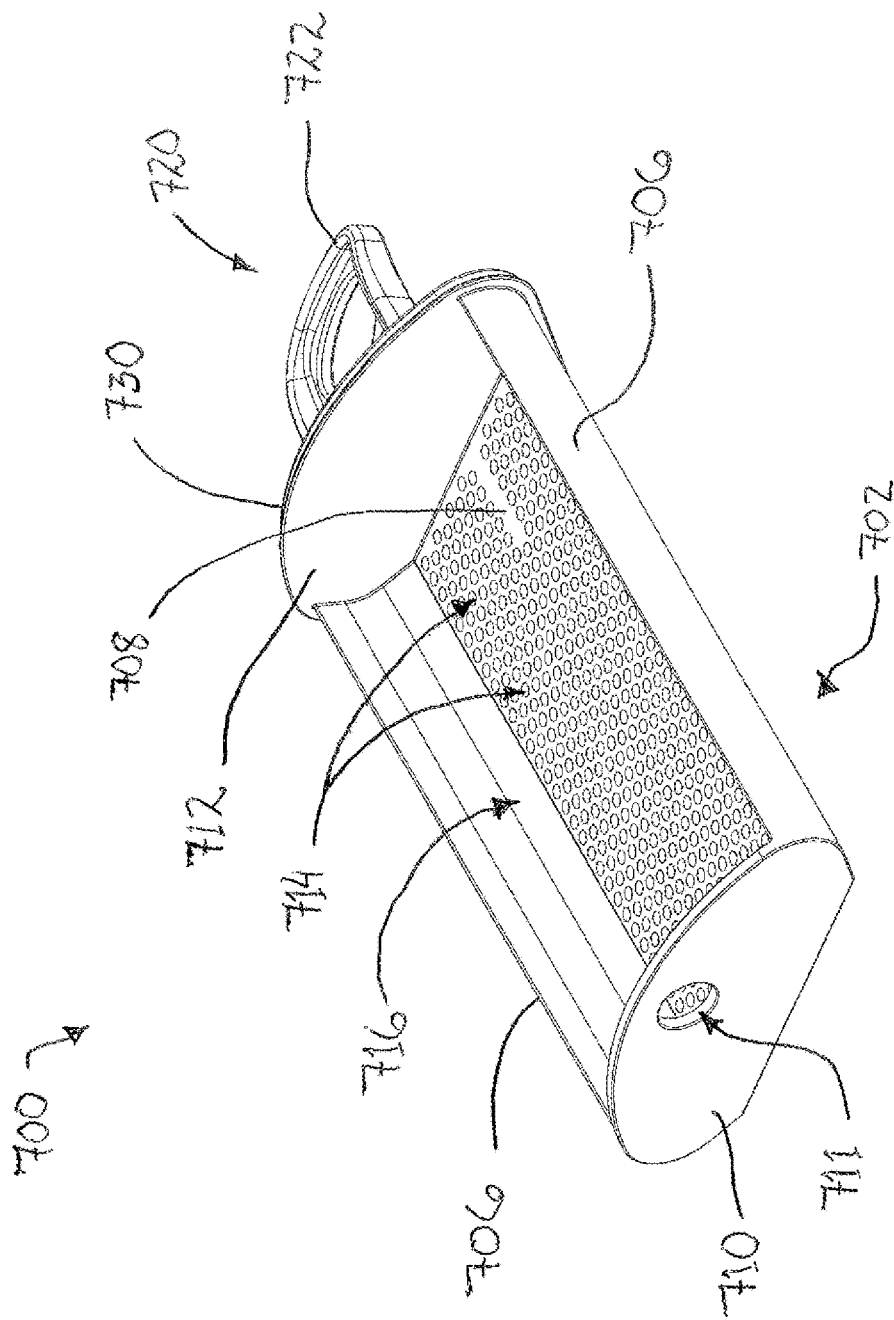
FIG. 23 depicts a perspective view of a bulk sample tray of the tissue sample holder of FIG. 17.

FIG. 23 shows bulk sample tray (700) in greater detail. As will be understood, bulk sample tray (700) is generally configured to receive a plurality of tissue samples therein. Bulk sample tray (700) comprises a tray portion (702), a handle portion (720), and a seal (730) disposed between tray portion (702) and handle portion (720). Tray portion (702) includes a strip (704) that defines a generally elongate oval-shaped cross-section that corresponds to the shape of at least a portion of bulk tray chamber (648) of rotatable member (630). Strip (704) further defines a front wall (710), a pair of sidewalls (706), a floor (708), and a back wall (712). Sidewalls (706), floor (708), front wall (710), and back wall (712) generally define a bulk tissue sample chamber (716) that is configured to receive a plurality of tissue samples though a tissue opening (711) in front wall (710).

To communicate vacuum to tissue sample chamber (716), floor (708) further includes a plurality of vacuum openings (714) that communicate between tissue sample chamber (716) and the exterior of bulk sample tray (700). As will be described in greater detail below, bulk sample tray (700) is configured to pull tissue samples though cutter (130) and into tissue sample chamber (716) when vacuum is applied though vacuum openings (714) and into tissue sample chamber (716).

Each side wall (706) curves outwardly relative to floor (708). The curvature of side walls (706) generally increases the volume of tissue sample chamber (716). In addition, the curvature of side walls (706) corresponds to the curvature defined by outer wall (632) and tray walls (646) of rotatable member (630). This correspondence between the shape of side walls (606) and the shape of walls (632, 646) permits walls (632, 646) to grip side walls (706) to thereby hold bulk sample tray (700) in position within rotatable member (630).

Handle portion (720) protrudes proximally from tray portion (702). Handle portion (720) is configured to permit an operator to manipulate bulk sample tray (700) to move bulk sample tray (700) relative to rotatable member (630). In particular, handle portion (720) includes a generally trapezoidal shaped grasping feature (722) that is configured for grasping by an operator. Although not shown, it should be understood that grasping feature (722) can include features to enhance an operator's grip when gripping grasping feature (722).

Seal (730) is disposed between tray portion (702) and handle portion (720). Seal (730) extends outwardly from the exterior of tray portion (702) to seal against outer wall (632) and tray walls (646) of rotatable member (630). As will be described in greater detail below, seal (730) is generally configured to promote the flow of vacuum from a given vacuum opening (654) of rotatable member (630), though vacuum openings (714) in floor (708) of tray portion (702) and out of tray portion (702) to cutter (130). Seal (730) of the present example is shown as outwardly extending flange that can be equipped with an O-ring or other sealing gasket. However, in other examples it should be understood that seal (730) may take on numerous alternative forms such as a wiper seal. Alternatively, in still other examples, seal (730) can be omitted entirely and be replaced with a sealing interference fit between tray portion (702) and walls (632, 646) of rotatable member (630).

FIG. 24 shows trays (648, 650) disposed within rotatable manifold (630). As can be seen, walls (632, 646) of rotatable member (630) are shaped to orient trays (648, 650) outwardly toward the outer perimeter of rotatable member (630). This creates a passage between floors (668, 708) of each tray (648, 650) and the inner portion of rotatable member (630). Each passage that is formed by this configuration is configured to promote the flow of vacuum into rotatable member (630) below floors (668, 708) and upwardly into each chamber (676, 716) defined by each tray (648, 650) to thereby transport a severed tissue sample into each tray (648, 650).

FIGS. 17 and 25A-25C show an exemplary use of tissue sample holder (600) to collect tissue samples from biopsy device (10). As will be described in greater detail below, tissue sample holder (600) is generally configured such that an operator can rotate rotatable member (630) by directly grasping rotatable member (630) to selectively index individual sample tray (660) or any one of bulk sample trays (700) with cutter (130) to collect tissue samples. Such selectable indexing of tissue sample holder (600) provides selective transitioning of tissue sample holder (600) between an individual sample collection mode and a bulk sample collection mode. When in the individual sample collection mode, tissue sample holder (600) can provide an operator more flexibility with respect to tissue sample analysis. When in the bulk sample collection mode, tissue sample holder (600) can provide an operator with the ability to collect a relatively large number of tissue samples without having to replace or otherwise empty trays (700). Although various methods of using these two modes in connection with a biopsy procedure are described herein, it should be understood that numerous other methods may be used as will be apparent to those of ordinary skill in the art in view of the teachings herein.

In one merely exemplary use, an operator may begin a biopsy procedure with tissue sample holder (600) in the individual sample collection mode as shown in FIG. 17. In some uses, tissue sample holder (600) is transitioned to the individual sample collection mode prior to beginning the biopsy procedure. Alternatively, tissue sample holder (600) is set to the individual sample collection mode after placement of needle (110) within a patient, but prior to initiation of tissue sample collection via cutter (130). In either case, it should be understood that in the present mode of operation, tissue sample holder (600) is set to the individual sample collection mode so that a first sample acquired by cutter (130) is transported into individual sample tray (660) rather than any one of bulk trays (700). In this method of use, an operator may be permitted to analyze the first sample to verify a desired positioning of needle (110) within a patient or otherwise conduct some preliminary analysis of the first tissue sample.

In the present use example, tissue sample holder (600) is transitioned to the individual sample collection mode by an operator grasping rotatable member (630) and rotating rotatable member (630) in a clockwise or counter clockwise direction. This rotation of rotatable member (630) results in corresponding rotation of sample trays (660, 700), which are disposed within rotatable member (630). Rotation of rotatable member (630) continues until individual sample tray (660) is positioned in a "twelve o'clock" position, corresponding to the position shown in FIG. 17. In this position, individual sample tray (660) is aligned with cutter (130) such that tissue samples received by tissue sample holder (600) from cutter (130) are received within individual sample tray (660).

Once tissue sample holder (600) is transitioned to the individual sample collection mode as shown in FIG. 17, the first tissue sample may be acquired by actuating cutter (130) relative to cannula (113) to sever the first tissue sample. Vacuum is next applied to the vacuum opening (654) associated with individual tray chamber (650). This application of vacuum induces a negative pressure within the interior of rotatable member (630). This negative pressure flows into tissue sample chamber (676) of individual sample tray (660) via vacuum openings (674) in floor (668) of individual sample tray (660). Vacuum then flows from tissue sample chamber (676) of individual sample tray (660) to cutter (130) to thereby transport the first tissue sample proximally though cutter and into tissue sample chamber (676) of individual sample tray (660). Venting may be applied to the distal face of the tissue sample within cutter (130) to thereby provide a pressure differential that results in proximal translation of the tissue sample through cutter (130) into tissue sample chamber (676).

Once the first tissue sample is received within individual sample tray (660), an operator may desire to inspect the first tissue sample. To inspect the first tissue sample, an operator grasps individual sample tray (660) via grasping feature (682) to pull individual sample tray (660) proximally and out of rotatable member (630). Once individual sample tray (660) is removed from rotatable member (630), the first tissue sample can be visually inspected. If an operator desires to touch, feel, or otherwise manipulate the first tissue sample, an operator may remove the first tissue sample from individual sample tray (660). In addition, or in the alternative, if an operator desires analysis beyond visual inspection, the first tissue sample can be removed from individual sample tray (660) and placed in another container for specimen radiograph or any other suitable preliminary tissue sample analysis modality.

Once preliminary analysis of the first tissue sample is complete, in some instances an operator may not be satisfied with the first tissue sample. For instance, as described above, the first tissue sample may be used to assess the positioning of needle (110) within a patient. If preliminary analysis of the first tissue sample indicates that the positioning of needle (110) within a patent is undesirable, an operator may desire to reposition needle (110) and acquire another sample for inspection. In this case, an operator may discard the first tissue sample, insert individual sample tray (660) back into rotatable member (630), and then repeat the steps described above to acquire a second tissue sample for preliminary analysis. This process may be repeated as many times as necessary until an operator is satisfied with a tissue sample collected within individual sample tray (660).

Figure 25A:
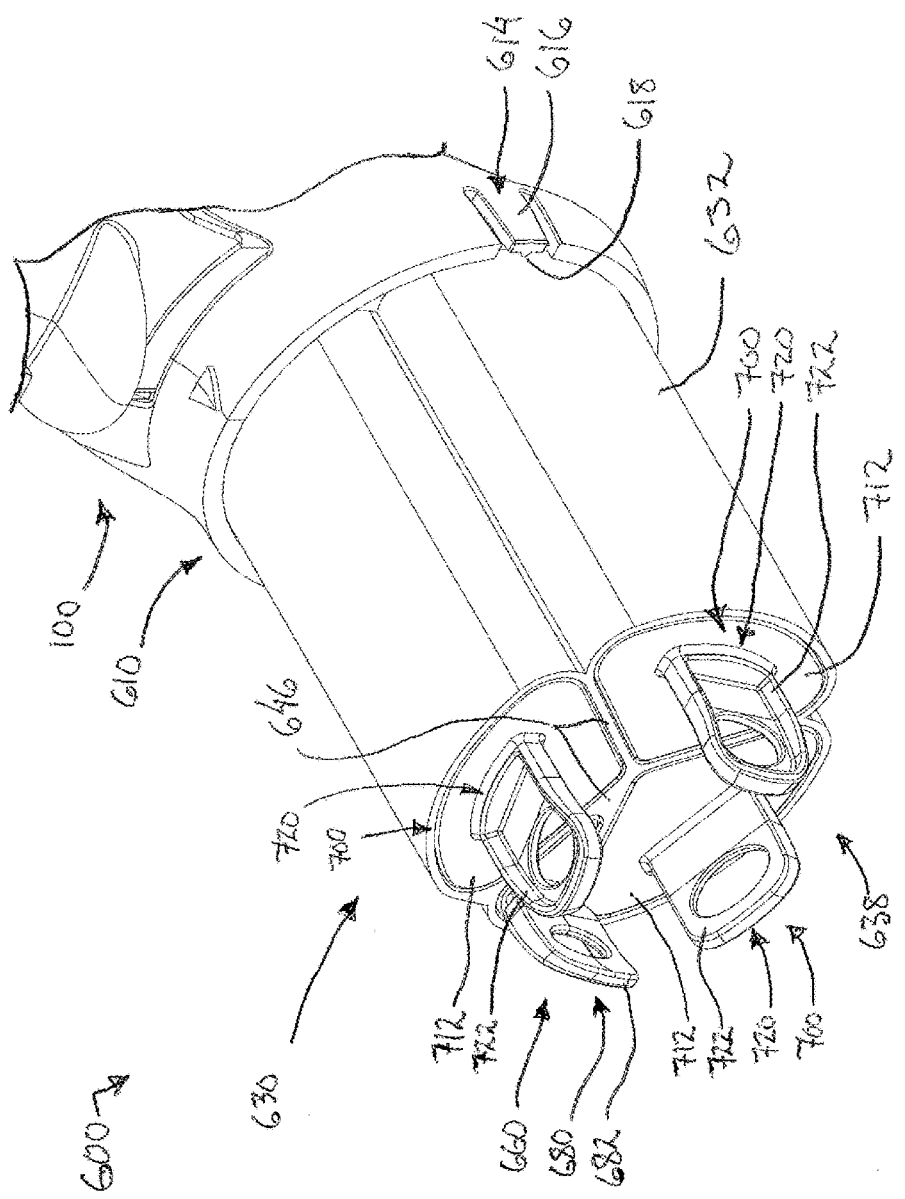
FIG. 25A depicts another perspective view of the tissue sample holder of FIG. 17, with the tissue sample holder in a first bulk sample collection position.

Once an operator is satisfied with the first tissue sample, or any other subsequent sample acquired with individual sample tray (660) thereafter, an operator may next desire to acquire tissue samples in the bulk sample collection mode. To transition tissue sample holder (600) to the bulk collection mode, an operator grasps rotatable member (630) to rotate rotatable member (630) in a clockwise or counter clockwise direction. Rotation continues until any one of bulk sample trays (700) are positioned in the twelve o'clock position as shown in FIG. 25A. In the position shown in FIG. 25A, a selected bulk sample tray (700) is indexed with cutter (130) to receive tissue samples therein when severed by cutter (130).

Once rotatable member (630) of tissue sample holder (600) is rotated to index a selected bulk sample tray (700) with cutter (130), tissue sample holder (600) is transitioned to the bulk sample collection mode. In the bulk sample collection mode, an operator can collect a plurality of tissue samples within each bulk sample tray (700). For instance, tissue samples can be severed by actuating cutter (130) relative to cannula (113) of needle (110). Once each tissue sample is severed, vacuum is applied to tissue sample holder (600) via the vacuum opening (654) associated with the selected bulk sample tray (700). The vacuum applied to vacuum opening (654) then flows into rotatable member (630), into tissue sample chamber (716) of the selected bulk sample tray (700), through tissue opening (711), and into cutter (130). This flow of vacuum creates a fluid circuit that transports each tissue sample severed by cutter (130) though cutter (130) and into tissue sample chamber (716) of the selected bulk sample tray (700). As noted above, venting may be applied to the distal face of the tissue sample within cutter (130) to thereby provide a pressure differential that results in proximal translation of the tissue sample through cutter (130) into tissue sample chamber (716).

Tissue samples can be continued to be collected until the selected bulk sample tray (700) reaches its sample capacity. Although the particular sample capacity may vary by a number of factors such as the particular dimensions of tissue sample holder (600) or the gauge of needle (110), in some examples each bulk sample tray (700) can receive anywhere between 10-20 tissue samples.

Regardless of the particular capacity of each bulk sample tray (700), once the selected bulk sample tray (700) is full, an operator may continue collecting tissue samples in the bulk collection mode by grasping rotatable member (630) and rotating rotatable member (630) to index another bulk sample tray (700) with cutter (130) as shown in FIG. 25B. Tissue sample collection may continue until two of the three bulk sample trays (700) are filled to capacity.

Once two of the three bulk sample trays (700) are filled to capacity, an operator can continue collecting samples in the bulk collection mode by rotating tissue sample holder (600) as described above to position tissue sample holder (600) as shown in FIG. 25C. This positions the third and final bulk sample tray (700) into communication with cutter (130) to receive severed tissue samples as they are severed by cutter (130). Bulk tissue sample collection can continue until all three bulk sample trays (700) are filled.

Once all bulk sample trays (700) are filled, an operator can simply finalize the biopsy procedure by removing needle (110) from a patient and performing other finalizing steps. Alternatively, in some uses an operator may desire to conduct further tissue sample analysis. For instance, in some uses, an operator may desire to analyze one or more tissue samples to determine if an entire lesion was removed during bulk collection. To engage in further analysis, an operator can return tissue sample holder (600) to the individual collection mode described above by rotating tissue sample holder (600) to the position shown in FIG. 17. Once in the individual sample mode, an operator may collect a tissue sample and conduct a visual analysis or other form of analysis as described above by removing individual sample tray (660) from rotatable member (630). This process of individual tissue sample analysis may then be repeated until an operator obtains satisfactory results.

If an operator desires to collect additional bulk samples after analysis of one or more individual samples, the operator may transition tissue sample holder (600) back to bulk collection mode as described above. If all bulk sample trays (700) are full at this stage, an operator may remove one or more bulk sample trays (700) to empty the one or more bulk sample trays (700). Bulk tissue collection may then continue until a desired number of tissue samples have been collected.

Although not described above, it should be understood that at any time during bulk sample collection an operator may selectively switch between bulk sample collection mode and individual sample collection mode. This may be desirable to engage in intermediate procedure individual sample analysis via individual sample collection mode. For instance, in some uses an operator may use bulk sample collection mode to remove an entire lesion from a patient. Thus, it may be desirable to periodically check progress toward this end using individual sample collection mode. In such a use, if a visual inspection via individual collection mode indicates suspect tissue, an operator may return to bulk sample collection mode to collect additional samples. However, if a visual inspection via individual collection mode indicates no suspect tissue, an operator may conclude that adequate samples have been taken and the procedure may be finalized.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy device comprising: a body; a needle extending distally from the body; a cutter longitudinally translatable relative to the needle, wherein the cutter defines a cutter lumen; and a tissue sample holder including, an outer cup, a rotatable member, wherein the rotatable member defines an inner chamber partially divided by a plurality of tray protrusions extending radially inwardly from a cylindrical wall of the rotatable member, wherein each tray protrusion of the plurality of tray protrusions defines a radial extension length, wherein each tray protrusion of the plurality of tray protrusions curves axially along the radial extension length of each tray protrusion, an individual sample tray comprising a single sample chamber, wherein the single sample chamber is configured to receive a single tissue sample, and one or more bulk sample trays, wherein the bulk sample tray is configured to receive a plurality of tissue samples.

Example 2

The biopsy device of Example 1, wherein the rotatable member includes a proximal wall, wherein the proximal wall includes an individual tray opening and one or more bulk tray openings, wherein the individual sample tray is configured to be received within the individual tray opening, wherein each bulk sample tray of the one or more bulk sample trays is configured to be received within a corresponding bulk tray opening.

Example 3

The biopsy device of Example 2, wherein a pair of tray protrusions of the rotatable member are positioned to align with the individual tray opening and the one or more bulk tray openings.

Example 4

The biopsy device of any one or more of Examples 1 through 3, wherein the individual sample tray includes a tray portion, wherein each bulk sample tray of the one or more bulk sample trays comprises a tray portion.

Example 5

The biopsy device of Example 4, wherein the tray protrusions of the rotatable member are configured to secure the tray portion of the individual sample tray and the tray portion of each bulk sample tray within the rotatable member.

Example 6

The biopsy device of any one or more of Examples 1 through 5, wherein each bulk chamber of the one or more bulk chambers comprises a pair of sidewalls, a back wall, and a floor.

Example 7

The biopsy device of Example 6, wherein the floor is V-shaped, wherein the floor comprises a plurality of vacuum openings, wherein the vacuum openings are evenly spaced about the entire V-shape of the floor.

Example 8

The biopsy device of any one or more of Examples 1 through 7, wherein the tissue sample holder further includes a manual rotation wheel.

Example 9

The biopsy device of Example 8, wherein the manual rotation wheel includes a resilient feature, wherein the resilient feature is configured to engage at least a portion of the outer cup to bias the rotatable member towards a plurality of predetermined positions.

Example 10

The biopsy device of Example 8, wherein the manual rotation wheel is coupled to the rotatable member such that the rotation member is manually rotatable to index the individual sample tray and each bulk sample tray of the one or more bulk sample trays with the cutter.

Example 11

A biopsy device comprising: a body; a needle extending distally from the body; a cutter longitudinally translatable relative to the needle, wherein the cutter defines a cutter lumen; and a tissue sample holder including, a rotatable member, wherein at least a portion of the rotatable member defines an inner chamber partially divided by a plurality of tray protrusions extending radially inwardly from a cylindrical wall of the rotatable member, an individual sample tray including a single sample chamber, wherein the single sample chamber is configured to receive only a single tissue sample, and one or more bulk sample trays, wherein the bulk sample tray is configured to receive a plurality of tissue samples.

Example 12

The biopsy device of Example 11, wherein the rotatable member includes a plurality of tray walls that define a plurality of discrete tray chambers within the inner chamber defined by at least a portion of the rotatable member.

Example 13

The biopsy device of Example 12, wherein the plurality of discrete tray chambers includes an individual tray chamber and a bulk tray chamber, wherein the individual tray chamber is configured to receive the individual sample tray, wherein the bulk tray chamber is configured to receive a single bulk sample tray of the one or more bulk sample trays.

Example 14

The biopsy device of Example 13, wherein the rotatable member includes an outer wall, wherein the tray walls are integral to the outer wall.

Example 15

The biopsy device of Example 14, wherein the tray walls extend radially inwardly relative to the outer wall such that each tray wall connects to the other tray walls.

Example 16

The biopsy device of Example 14, wherein the outer wall defines a generally cylindrical cross-section interrupted by a series of outward and inward projections, the outward and inward projections corresponding to each tray wall of the plurality of tray walls.

Example 17

The biopsy device of any one or more of Examples 11 through 16, wherein the rotatable member includes a flange extending outwardly from at least a portion of the rotatable member.

Example 18

The biopsy device of Example 17, wherein the flange is configured to mate within a channel defined by a coupler associated with the probe such that the flange is configured to axially couple the rotatable member to the probe while permitting rotation of the rotatable member relative to the probe.

Example 19

The biopsy device of Examples 17 or 18, wherein the flange includes a plurality of locators, wherein each locator of the plurality of locators corresponds to the individual sample tray or a single bulk sample tray of the one or more bulk sample trays.

Example 20

The biopsy device of Example 19, wherein each locator comprises an indentation in the flange, the indentation having a triangular shape.

Example 21

The biopsy device of Example 19, further comprising an indexer, wherein the indexer is associated with the probe, wherein the indexer is configured to selectively lock the rotatable member in a plurality of positions relative to probe via engagement with each locator of the plurality of locators.

Example 22

The biopsy device of Example 21, wherein the indexer includes a resilient portion and an indexing portion, wherein the resilient portion is configured to resiliently bias the indexing portion into engagement with each locator of the plurality of locators.

Example 23

The biopsy device of Example 22, wherein the indexing portion of the indexer defines a triangular shape corresponding to a triangular shape of each locator of the plurality of locators.

Example 24

The biopsy device of any one or more of Examples 11 through 23, wherein the tissue sample holder further includes an outer cup, wherein the outer cup is configured to enclose at least a portion of the rotatable member.

Example 25

The biopsy device of any one or more of Examples 11 through 24, wherein the rotatable member includes an open proximal end and a closed distal end, the closed distal end defining a plurality of sample openings configured to receive a tissue sample from the cutter and a plurality of vacuum openings configured to receive vacuum from the probe.

Example 26

The biopsy device of Example 25, wherein the closed distal end of the rotatable member defines a plurality of ribs disposed between each vacuum opening of the plurality of vacuum openings, wherein the plurality of ribs are configured to fluidly isolate each vacuum opening of the plurality of vacuum openings relative to the other vacuum openings.

Example 27

The biopsy device of Example 26, wherein the plurality of ribs together form an x-shaped pattern.

Example 28

The biopsy device of Example 25, wherein each vacuum opening of the plurality of vacuum openings is associated with a corresponding an individual sample tray or a bulk sample tray, wherein the vacuum opening associated with the individual sample tray includes an upwardly extending extension configured to promote the flow of vacuum through the vacuum opening.

Example 29

The biopsy device of Example 28, wherein the vacuum opening associated with the individual sample tray is adjacent to a step, wherein the step is configured to promote the flow of vacuum into the individual sample tray.

Example 30

A method for using a biopsy device, the method comprising: preparing a biopsy probe for a biopsy procedure, the biopsy probe including a probe body, a needle extending from the probe body, and a cutter translatable relative to the cutter for collecting one or more tissue samples; manually rotating a rotatable member of a tissue sample holder to align an individual sample tray disposed within the rotatable member into communication with the cutter of the biopsy probe; receiving a single tissue sample within the individual sample tray; removing the individual sample tray from the tissue sample holder to inspect a tissue sample received therein; and manually rotating the rotatable member of the tissue sample holder to align a bulk sample tray with the cutter of the biopsy probe to collect a plurality of tissue samples within the bulk sample tray.

Example 31

The method of Example 30, wherein the step of removing the individual sample tray from the tissue sample holder to inspect a tissue sample includes visual inspection of the tissue sample.

Example 32

The method of Example 30, wherein the step of removing the individual sample tray from the tissue sample holder to inspect a tissue sample includes palpitation of the tissue sample.

Example 33

The method of Example 30, further comprising manually rotating the rotatable member of the tissue sample holder after filling a bulk sample tray with a plurality of samples to align another bulk sample tray with the cutter of the biopsy probe to collect a plurality of tissue samples within the other bulk sample tray.

Example 34

The method of Example 30, further comprising, after removing the individual sample tray from the tissue sample holder, emptying the individual sample tray and inserting the individual sample tray back into the tissue sample holder.

Example 35

The method of Example 34, further comprising manually rotating the rotatable member to align the individual sample tray with the cutter of the biopsy probe after collecting a plurality of tissue samples within the bulk sample tray.

Example 36

The method of Example 35, further comprising removing the individual sample tray from the tissue sample holder to visually inspect another tissue sample after collecting a plurality of tissue samples within the bulk sample tray.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device comprising:
   (a) a body;
   (b) a needle extending distally from the body;
   (c) a cutter longitudinally translatable relative to the needle, wherein the cutter defines a cutter lumen; and
   (d) a tissue sample holder including,
      (i) a rotatable member, wherein at least a portion of the rotatable member defines an inner chamber divided by a plurality of tray walls extending radially inwardly from an outer wall of the rotatable member,
      (ii) an individual sample tray including a single sample chamber, wherein the single sample chamber is configured to receive only a single tissue sample, and
      (iii) one or more bulk sample trays, wherein the bulk sample tray is configured to receive a plurality of tissue samples, wherein each bulk sample tray includes a distal end wall having a single sample opening for receiving tissue samples therethrough.

2. The biopsy device of claim 1, wherein the plurality of tray walls define a plurality of discrete tray chambers within the inner chamber defined by at least a portion of the rotatable member, wherein the plurality of discrete tray chambers includes an individual tray chamber and a bulk tray chamber, wherein the individual tray chamber is configured to receive the individual sample tray, wherein the bulk tray chamber is configured to receive a single bulk sample tray of the one or more bulk sample trays.

3. The biopsy device of claim 2, wherein the tray walls are integral to the outer wall.

4. The biopsy device of claim 3, wherein the tray walls extend radially inwardly relative to the outer wall such that each tray wall connects to the other tray walls.

5. The biopsy device of claim 3, wherein the outer wall defines a generally cylindrical cross-section interrupted by a series of outward and inward projections, the outward and inward projections corresponding to each tray wall of the plurality of tray walls.

6. The biopsy device of claim 1, wherein the rotatable member includes a flange extending outwardly from at least a portion of the rotatable member, wherein the flange is configured to mate within a channel defined by a coupler associated with the probe such that the flange is configured to axially couple the rotatable member to the probe while permitting rotation of the rotatable member relative to the probe.

7. The biopsy device of claim 6, wherein the coupler is configured to permanently and non-removably hold the rotatable member to the probe once the flange is received within the channel.

8. The biopsy device of claim 6, wherein the flange includes a plurality of locators, wherein each locator of the plurality of locators corresponds to the individual sample tray or a single bulk sample tray of the one or more bulk sample trays.

9. The biopsy device of claim 8, wherein each locator comprises an indentation in the flange, the indentation having a triangular shape.

10. The biopsy device of claim 8, further comprising an indexer, wherein the indexer is associated with the probe, wherein the indexer is configured to selectively lock the rotatable member in a plurality of positions relative to probe via engagement with each locator of the plurality of locators.

11. The biopsy device of claim 10, wherein the indexer includes a resilient portion and an indexing portion, wherein the resilient portion is configured to resiliently bias the indexing portion into engagement with each locator of the plurality of locators.

12. The biopsy device of claim 1, wherein the tissue sample holder further includes an outer cup, wherein the outer cup is configured to enclose at least a portion of the rotatable member.

13. The biopsy device of claim 1, wherein the rotatable member includes an open proximal end and a closed distal end, the closed distal end defining a plurality of sample openings configured to receive a tissue sample from the cutter and a plurality of vacuum openings configured to receive vacuum from the probe.

14. The biopsy device of claim 13, wherein the closed distal end of the rotatable member further defines a plurality of ribs, wherein the ribs extend between each sample opening and a vacuum opening associated with each sample opening to fluidly isolate each sample opening relative to other sample openings when the rotatable member is coupled to the probe.

15. A biopsy device comprising:
(a) a body;
(b) a needle extending distally from the body;
(c) a cutter longitudinally translatable relative to the needle, wherein the cutter defines a cutter lumen; and
(d) a tissue sample holder including,
(i) a rotatable member, wherein the rotatable member defines an inner chamber divided by a plurality of tray walls extending radially inwardly from an outer wall of the rotatable member, wherein each tray wall of the plurality of tray walls intersects with an inwardly oriented indentation of the outer wall,
(ii) an individual sample tray including a single sample chamber, wherein the single sample chamber is configured to receive a single tissue sample, and
(iii) one or more bulk sample trays, wherein the bulk sample tray is configured to receive a plurality of tissue samples.

16. The biopsy device of claim 15, wherein the rotatable member includes a proximal wall, wherein the proximal wall includes an individual tray opening and one or more bulk tray openings, wherein the individual sample tray is configured to be received within the individual tray opening, wherein each bulk sample tray of the one or more bulk sample trays is configured to be received within a corresponding bulk tray opening.

17. The biopsy device of claim 1, wherein each bulk chamber of the one or more bulk chambers includes a pair of sidewalls, a back wall, and a floor, wherein the floor is V-shaped, wherein the floor includes a plurality of vacuum openings, wherein the vacuum openings are evenly spaced about the entire V-shape of the floor.

18. The biopsy device of claim 1, wherein the tissue sample holder further includes a manual rotation wheel, wherein the manual rotation wheel includes a resilient feature, wherein the resilient feature is configured to engage at least a portion of the-rotatable member to bias the rotatable member towards a plurality of predetermined positions.

19. A method for using a biopsy device, the method comprising:
(a) preparing a biopsy probe for a biopsy procedure, the biopsy probe including a probe body, a needle extending from the probe body, and a cutter translatable relative to the probe body for collecting one or more tissue samples;
(b) manually rotating a rotatable member of a tissue sample holder to align an individual sample tray disposed within the rotatable member into communication with the cutter of the biopsy probe;
(c) receiving a single tissue sample within the individual sample tray;
(d) removing the individual sample tray from the tissue sample holder to inspect a tissue sample received therein; and
(e) manually rotating the rotatable member of the tissue sample holder to align a bulk sample tray with the cutter of the biopsy probe to collect a plurality of tissue samples within the bulk sample tray after inspecting the single tissue sample received within the individual sample tray.

20. The biopsy device of claim 1, wherein each bulk sample tray further includes a floor defining a flat bottom and having a plurality of vacuum openings.

* * * * *